United States Patent
Ries et al.

(10) Patent No.: US 9,675,399 B2
(45) Date of Patent: Jun. 13, 2017

(54) PATIENT SPECIFIC IMPLANTS AND INSTRUMENTATION FOR PATELLAR PROSTHESES

(71) Applicant: Michael D. Ries, Tiburon, CA (US)

(72) Inventors: Michael D. Ries, Tiburon, CA (US);
Bjorn N. Rindal, Chandler, AZ (US);
Joshua A. Butters, Chandler, AZ (US);
Nicholas Slater, Chandler, AZ (US)

(73) Assignee: Michael D. Ries, Reno, NV (US)

( * ) Notice: Subject to any disclaimer, the term of this patent is extended or adjusted under 35 U.S.C. 154(b) by 788 days.

(21) Appl. No.: 13/761,629

(22) Filed: Feb. 7, 2013

(65) Prior Publication Data
US 2013/0165939 A1    Jun. 27, 2013

Related U.S. Application Data

(63) Continuation-in-part of application No. 13/367,278, filed on Feb. 6, 2012, now Pat. No. 8,945,135, which
(Continued)

(51) Int. Cl.
*A61B 17/88* (2006.01)
*A61B 17/16* (2006.01)
(Continued)

(52) U.S. Cl.
CPC ........ *A61B 17/8863* (2013.01); *A61B 17/158* (2013.01); *A61B 17/1677* (2013.01); *A61B 17/1767* (2013.01); *A61B 2090/062* (2016.02)

(58) Field of Classification Search
CPC ..... A61B 17/15; A61B 17/154; A61B 17/158; A61B 17/1659; A61B 17/1675;
(Continued)

(56) References Cited

U.S. PATENT DOCUMENTS

| 3,878,566 A | 4/1975 | Bechtol |
| 3,927,423 A | 12/1975 | Swanson |

(Continued)

FOREIGN PATENT DOCUMENTS

| EP | 575232 | 2/1995 |
| EP | 474320 | 7/1995 |

(Continued)

OTHER PUBLICATIONS

Corrected Notice of Allowability dated Dec. 12, 2014 in U.S. Appl. No. 13/367,278.
(Continued)

*Primary Examiner* — Kevin T Truong
*Assistant Examiner* — Tracy Kamikawa
(74) *Attorney, Agent, or Firm* — Snell & Wilmer L.L.P.

(57) ABSTRACT

Patient specific implants and instrumentation for replacing a portion of a patella. Methods for producing patient specific implants and instrumentation include conducting imaging studies of the patient's native patella, deriving measurements of the patella and surrounding soft tissues from the imaging studies, manufacturing customized implants and instrumentation specific to the derived measurements, and implanting a customized implant using the customized instrumentation. Patient specific instrumentation includes: a patellar clamp ring, an anterior clamp, a restraining arm, a posterior clamping surface, a dual bore reaming collet, a reamer, a reaming depth gauge, and a resection cutting guide. Patient specific portions of a patellar implant include: topography of the posterior articular surface, facet angle, shape and dimensions of the anterior attachment surface, implant length, implant width, implant thickness and the outer perimeter shape of the implant.

14 Claims, 27 Drawing Sheets

Related U.S. Application Data is a continuation-in-part of application No. 13/367,192, filed on Feb. 6, 2012, now Pat. No. 8,747,478.

(60) Provisional application No. 61/596,104, filed on Feb. 7, 2012, provisional application No. 61/442,661, filed on Feb. 14, 2011, provisional application No. 61/479,173, filed on Apr. 26, 2011, provisional application No. 61/512,296, filed on Jul. 27, 2011.

(51) Int. Cl.
*A61B 17/15* (2006.01)
*A61B 17/17* (2006.01)
*A61B 90/00* (2016.01)

(58) Field of Classification Search
CPC . A61B 17/1677; A61B 17/17; A61B 17/1735; A61B 17/1739; A61B 17/1764; A61B 17/1767
See application file for complete search history.

(56) References Cited

U.S. PATENT DOCUMENTS

| | | | |
|---|---|---|---|
| 4,039,266 A | 8/1977 | O'Connell | |
| 4,158,894 A | 6/1979 | Worrell | |
| 4,565,192 A | 1/1986 | Shapiro | |
| 4,633,862 A | 1/1987 | Petersen | |
| 4,706,660 A | 11/1987 | Petersen | |
| 4,710,075 A | 12/1987 | Davison | |
| 4,944,756 A | 7/1990 | Kenna | |
| 5,021,055 A | 6/1991 | Burkinshaw | |
| 5,108,401 A | 4/1992 | Insall | |
| 5,129,907 A | 7/1992 | Heldreth | |
| 5,129,908 A | 7/1992 | Petersen | |
| 5,147,365 A | 9/1992 | Whitlock | |
| 5,180,384 A | 1/1993 | Mikhail | |
| 5,222,955 A | 6/1993 | Mikhail | |
| 5,236,462 A | 8/1993 | Mikhail | |
| 5,284,482 A | 2/1994 | Mikhail | |
| 5,306,278 A | 4/1994 | Dahl et al. | |
| 5,312,411 A | 5/1994 | Steele et al. | |
| 5,342,364 A | 8/1994 | Mikhail | |
| 5,383,937 A | 1/1995 | Mikhail | |
| 5,437,676 A | 8/1995 | Bouraly | |
| 5,480,443 A | 1/1996 | Elias | |
| 5,486,177 A | 1/1996 | Mumme | |
| 5,520,692 A | 5/1996 | Ferrante | |
| 5,522,901 A | 6/1996 | Thomas | |
| 5,536,271 A | 7/1996 | Daly | |
| 5,575,793 A | 11/1996 | Carls | |
| 5,580,353 A | 12/1996 | Mendes | |
| 5,593,450 A | 1/1997 | Scott | |
| 5,609,640 A | 3/1997 | Johnson | |
| 5,609,644 A | 3/1997 | Ashby et al. | |
| 5,616,146 A | 4/1997 | Murray | |
| 5,690,637 A | 11/1997 | Wen | |
| 5,702,467 A | 12/1997 | Gabriel | |
| 5,716,360 A | 2/1998 | Baldwin | |
| 5,824,099 A | 10/1998 | Mendes | |
| 5,871,540 A | 2/1999 | Weissman | |
| 5,885,298 A | 3/1999 | Herrington | |
| 5,941,884 A | 8/1999 | Corvelli | |
| 6,080,162 A | 6/2000 | Dye | |
| 6,146,423 A | 11/2000 | Cohen | |
| 6,159,246 A | 12/2000 | Mendes | |
| 6,190,415 B1 | 2/2001 | Cooke | |
| 6,277,121 B1 | 8/2001 | Burkinshaw | |
| 6,602,258 B1 | 8/2003 | Katz | |
| 6,602,292 B2 | 8/2003 | Burkinshaw | |
| 6,800,094 B2 | 10/2004 | Burkinshaw | |
| 6,802,864 B2 | 10/2004 | Tornier | |
| 6,866,667 B2 | 3/2005 | Wood | |
| 6,913,463 B2 | 7/2005 | Blacklock | |
| 7,316,687 B2 | 1/2008 | Aikins et al. | |
| 7,344,540 B2 | 3/2008 | Smucker | |
| 7,468,075 B2 | 12/2008 | Lang | |
| 7,534,263 B2* | 5/2009 | Burdulis, Jr. | A61B 17/155 606/88 |
| 7,566,335 B1* | 7/2009 | Scott | A61B 17/158 606/88 |
| 7,604,639 B2 | 10/2009 | Swanson | |
| 7,618,451 B2 | 11/2009 | Berez | |
| 7,713,305 B2 | 5/2010 | Ek | |
| 7,758,651 B2 | 7/2010 | Chauhan | |
| 7,799,077 B2 | 9/2010 | Lang | |
| 7,981,158 B2 | 7/2011 | Fitz | |
| 8,105,330 B2 | 1/2012 | Fitz | |
| 8,123,699 B2 | 2/2012 | Lyon | |
| 8,187,282 B2 | 5/2012 | Tornier et al. | |
| 8,308,781 B2 | 11/2012 | Wilson | |
| 2003/0120346 A1 | 6/2003 | Mercinek | |
| 2005/0015092 A1 | 1/2005 | Rathbun et al. | |
| 2007/0118141 A1 | 5/2007 | Marchyn | |
| 2007/0162142 A1 | 7/2007 | Stone | |
| 2007/0198022 A1 | 8/2007 | Lang | |
| 2008/0027458 A1 | 1/2008 | Aikins et al. | |
| 2008/0188855 A1 | 8/2008 | Brown et al. | |
| 2008/0300689 A1 | 12/2008 | McKinnon | |
| 2009/0036993 A1 | 2/2009 | Metzger | |
| 2009/0222103 A1 | 9/2009 | Fitz | |
| 2009/0326661 A1 | 12/2009 | Wright | |
| 2009/0326662 A1 | 12/2009 | Goldstein | |
| 2010/0030223 A1 | 2/2010 | Keller | |
| 2010/0057211 A1 | 3/2010 | Cuckler | |
| 2010/0131068 A1 | 5/2010 | Brown et al. | |
| 2010/0160915 A1 | 6/2010 | Chauhan | |
| 2010/0160917 A1 | 6/2010 | Fitz | |
| 2010/0174379 A1 | 7/2010 | McMinn | |
| 2010/0191245 A1 | 7/2010 | Ek et al. | |
| 2010/0241237 A1 | 9/2010 | Pappas | |
| 2010/0305574 A1 | 12/2010 | Fitz | |
| 2011/0029093 A1 | 2/2011 | Bojarski | |
| 2011/0066193 A1 | 3/2011 | Lang | |
| 2013/0030539 A1* | 1/2013 | Wright | A61B 17/1767 623/20.18 |

FOREIGN PATENT DOCUMENTS

| | | |
|---|---|---|
| EP | 676182 | 10/1995 |
| WO | WO9410914 | 5/1994 |
| WO | 9413214 | 6/1994 |
| WO | WO9625115 | 8/1996 |

OTHER PUBLICATIONS

Notice of Allowance dated Nov. 25, 2014 in U.S. Appl. No. 13/367,278.
Office Action dated Jun. 21, 2013 in U.S. Appl. No. 13/367,192.
Notice of Allowance dated Jan. 27, 2014 in U.S. Appl. No. 13/367,192.
International Search Report dated Jun. 13, 2012 in Application No. PCT/US2012/024026.
Written Opinion dated Jun. 13, 2012 in Application No. PCT/US2012/024026.
International Preliminary Report on Patentability dated Aug. 21, 2013 in Application No. PCT/US2012/024026.
Baldwin, Anatomic Dimensions of the Patella Measured During Total Knee Arthroplasty, Journal of Arthroplasty vol. 20 No. 2, 2005.
Hitt, Anthropometric Measurements of the Human Knee: Correlation to the Sizing of Current Knee Arthroplasty Systems, The Journal of Bone and Joint Surgery col. 85-A supplement 4, 2003.
Dennis, The John Insall Award, Control-Matched Evaluation of Painful Patellar Crepitus after Total Knee Arthroplasty, Clinic of Orthop Related Research, 2011, 469:10-17.
Smith & Nephew, Knee System Catalog, Oct. 16, 2003.
Waldemar Link, Lubinus Total Patella Glide Replacement Prosthesis, 705d-en/3.91, 1978.
Hoffmann, Patellar Component Medialization in Total Knee Arthroplasty, The Journal of Arthroplasty, vol. 12, No. 2, 1997.

(56) References Cited

OTHER PUBLICATIONS

Introna, Sex Determination by Discriminant Analysis of Patella Measurements, Forensic Science International 95, 1998, 39-45.
Erak, Ten Year Results of an Inset Biconvex Patella Prosthesis in Primary Knee Arthroplasty, Clinic Ortho Related Research, 2009, 467:1781-1792.
Erak, The Cemented Inset Biconvex Patella in Revision Knee Arthroplasty, The Knee 16, 2009, 211-215.
Jordan, The Long Term Results of Metal Backed Mobile Bearing Patella, Clinic Orthopaedics and Related Researd No. 436, pp. 11-118, 2005.
Iranpour, The Width: Thickness Ration of the Patella, Clinic Orthopaedic Related Research, 2008, 466, 1198-1203.
Hsu, Wear and Deformation of Patellar Components in Total Knee Arthroplasty, Clinical Orthopaedics and Related Research No. 246, Sep. 1989.
Restriction Requirement dated Jul. 18, 2013 in U.S. Appl. No. 13/367,278.
Office Action dated Oct. 24, 2013 in U.S. Appl. No. 13/367,278.
Final Office Action dated Jan. 2, 2014 in U.S. Appl. No. 13/367,278.
Advisory Action dated Mar. 28, 2014 in U.S. Appl. No. 13/367,278.
Smith & Nephew; Journey—Bi-Cruciate Stabilized Knee System; Surgical Technique, # 40490101 Mar. 2006.
Smith & Nephew; Journey Deuce Bi-Compartmental Knee System Surgical Technique #40960101 May 2007.
Smith & Nephew; Genesis II Total Knee System—Patella Large Reamer Resurfacing System, Surgical Technique 40420108 7128-1285 Mar. 2005.
Smith & Nephew; Minimally Invasive TKA Genesis II Anterior Cut First, Surgical Technique. #40420105 7128-1226 Nov. 2003.
Omega Surgical Instruments, Inc. Product Catalog. 2011 11.4.
Luis S. M. Gomes; Patellar Prosthesis Positioning in total Knee Arthroplasty (A Roentgenographic Study. Clinical Orthopaedics and Related Research p. 72-81 No. 236, Nov. 1988.
Smith & Nephew; Profix Total Knee System,Minimally Invasive TKA PROFIX Distal Cut First. Surgical Technique 40430103 7128-1257 Oct. 2004.
Smith & Nephew; PROFIX Surgical Technique. Jan. 1998 7128-0492.
Exam Report dated Dec. 3, 2014 in European Application No. 12704591.2.
Communication Under Rule 71(3) EPC dated Aug. 3, 2015 in European Application No. 12704591.2.
Patent Examination Report No. 1 dated Jun. 23, 2015 in Australian Application No. 2012218086.
Notice of Acceptance dated Sep. 25, 2015 in Australian Application No. 2012218086.
Examination Report dated Jul. 8, 2016 in Australian Application No. 2015210381.
Notice of Acceptance dated Oct. 4, 2016 in Australian Application No. 2015210381.

\* cited by examiner

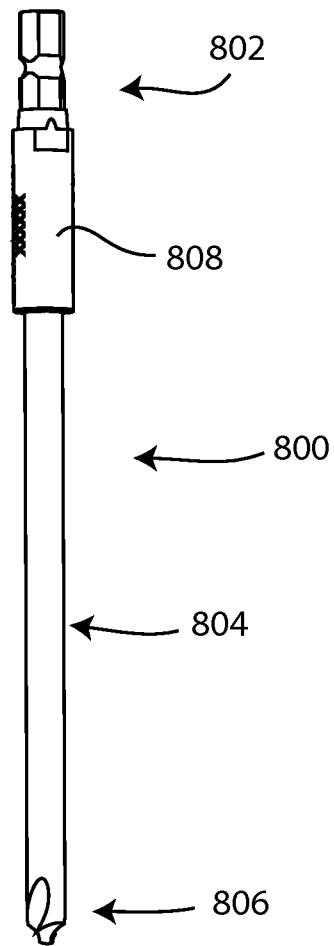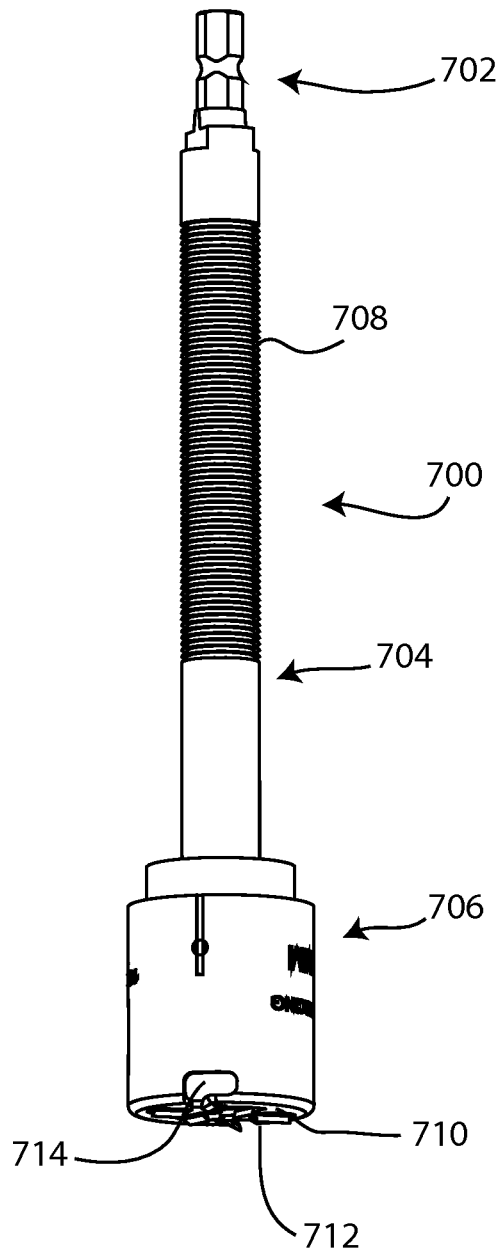
Fig. 7
Fig. 8

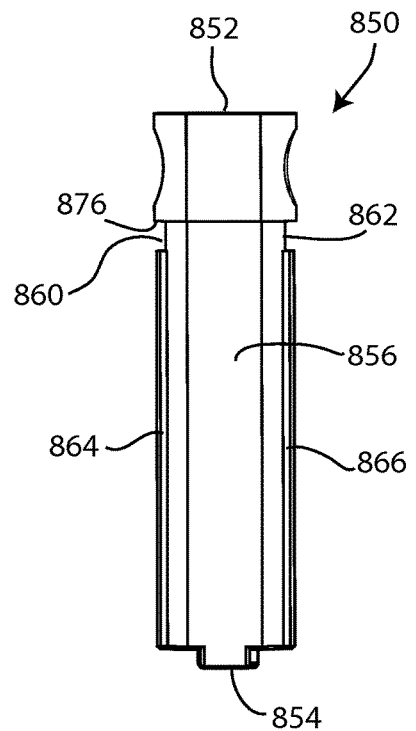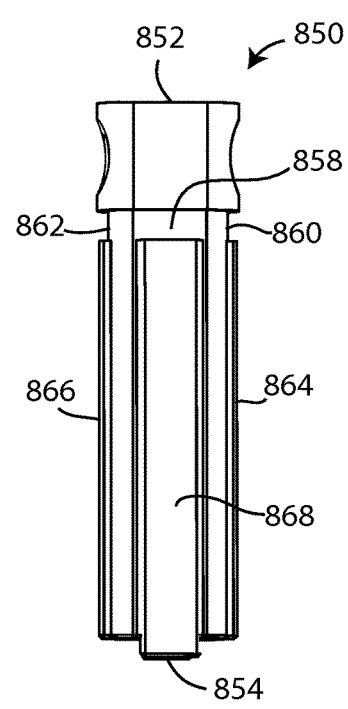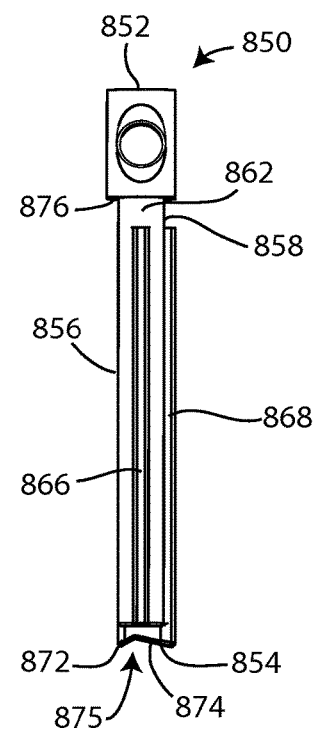
Fig. 11A    Fig. 11B    Fig. 11C
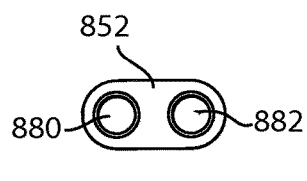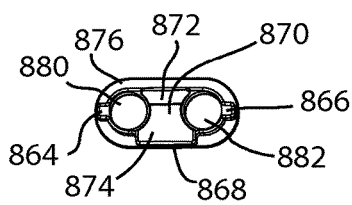
Fig. 11D    Fig. 11E

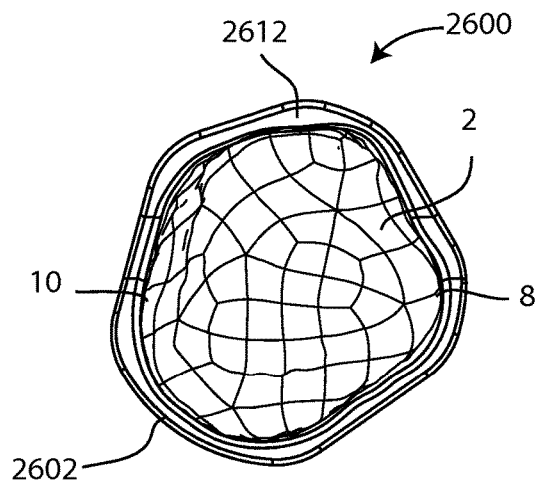
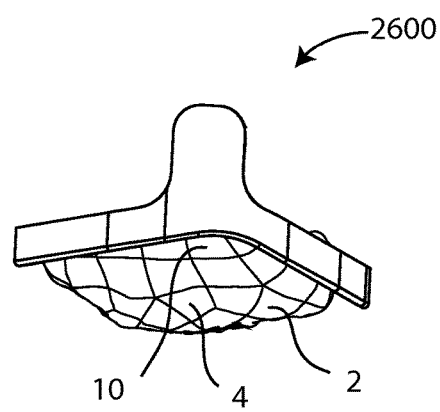
Fig. 30A          Fig. 30B
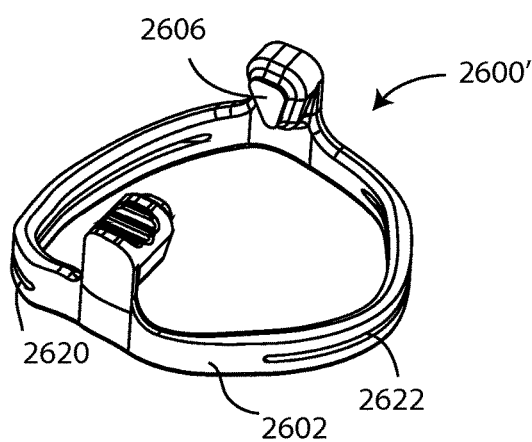
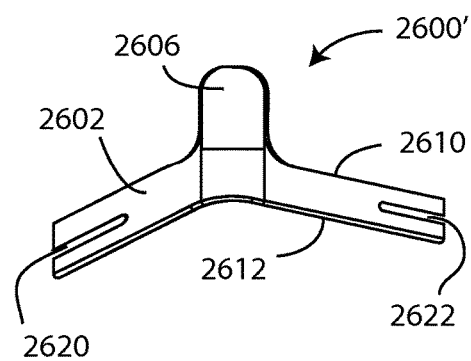
Fig. 31A          Fig. 31B

PATIENT SPECIFIC IMPLANTS AND INSTRUMENTATION FOR PATELLAR PROSTHESES

CROSS-REFERENCE TO RELATED APPLICATIONS

This application is a non-provisional of:

U.S. Provisional Patent Application No. 61/596,104, filed Feb. 7, 2012, and is entitled PATIENT SPECIFIC IMPLANTS AND INSTRUMENTATION FOR PATELLAR PROSTHESES.

This application is also a continuation-in-part of:

pending U.S. patent application Ser. No. 13/367,278, filed Feb. 6, 2012, and is entitled PATELLAR PROSTHESES AND INSTRUMENTATION, which application is a non-provisional of:

U.S. Provisional Patent Application No. 61/442,661, filed Feb. 14, 2011, and is entitled ANATOMIC PATELLAR PROSTHESIS; and U.S. Provisional Patent Application No. 61/479,173, filed Apr. 26, 2011, and is entitled INSTRUMENTS AND METHODS FOR MULTI-PLANAR PATELLAR PROSTHESES; and U.S. Provisional Patent Application No. 61/512,296, filed Jul. 27, 2011, and is entitled INSTRUMENTS AND METHODS FOR ORTHOPEDIC RESECTION.

Pending U.S. patent application Ser. No. 13/367,278 also claims priority to and benefit of pending U.S. patent application Ser. No. 13/367,192, filed Feb. 6, 2012 contemporaneously herewith, and is entitled PATELLAR PROSTHESES AND INSTRUMENTATION and which is owned by the same owner of this application.

The above-identified documents are incorporated herein by reference.

FIELD OF THE DISCLOSURE

This disclosure relates to systems, methods and instrumentation for total knee arthroplasty. More specifically, this disclosure relates to implantable patellar prostheses, instrumentation for patellar reaming and resection, and methods for patellar arthroplasty.

BACKGROUND OF THE INVENTION

Patellar arthroplasty may be performed to treat cartilage damage, arthritis, or injury to the patellofemoral joint. In a patellar arthroplasty, a portion of the patella is replaced with a patellar implant or prosthesis. The prosthesis may have a posterior-facing bearing surface for articulation with the natural medial and lateral condyles situated on the distal end of the femur, or for articulation with a femoral implant. An anterior surface of the implant anchors to the remaining natural or prepared patella.

Patellar implants known in the art include onlay and inset style implants. Patella reaming guides are used presently in patellar resurfacing procedures for both onlay and inset style patella implants. For onlay implants, an oversized reamer collet is used to surround the entire exposed posterior surface of the patella and resurface the complete posterior patella with one reaming step. For inset implants, a slightly smaller reamer collet is used to ream only a portion of the patella. Onlay implants may be oval shaped to approximate the exposed cut area. Alternatively, some onlay implants are smaller than the exposed area and leave a portion of the cut bone exposed, which may create problems with soft tissue ingrowth. Furthermore, onlay patellar implants may be more prone to migrating or loosening then inset implants. The reaming step used to prepare the patella for the onlay implant also does little to conserve the amount of bone volume remaining in the patella, which can lead to complications such as patellar fracture. While an inset "button" implant may completely cover the resurfaced portion of the bone, the smaller prosthesis area may not sufficiently remove all areas of diseased cartilage and the patient may be left with pathology. Need exists for patellar implants and bone preparation instrumentation which conserve bone volume while also allowing for removal of all areas of diseased cartilage.

Patellar implants known in the art include a single flat, or uni-planar, anterior surface for anchoring to patellar bone. A single flat anchoring surface may not provide resistance to shear loads, and may therefore be more prone to loosening and migration. Need exists for implants with geometry that leverages two or more non-parallel surfaces at the bone-contacting interface, in order to provide better resistance to shear loads and be more resistant to loosening and migration. Having two or more planes at the bone-contacting interface allows the patella to be prepared to better match the native patella geometry, and may contribute to patellar bone conservation. In addition, better overall coverage of the articular surface may be provided by an implant having two or more planes at the bone-contacting interface. Instrumentation and methods for preparing a multi-planar prepared bone surface for receiving an implant with a multi-planar anchoring surface are also needed.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 7 is a side view of the drill of FIG. 5;

FIG. 8 is a side view of the reamer of FIG. 5;

FIG. 11A is a medial side view of the drill guide of FIG. 5; FIG. 11B is a lateral side view of the drill guide of FIG. 11A; FIG. 11C is another side view of the drill guide of FIG. 11A; FIG. 11D is a top view of the drill guide of FIG. 11A; FIG. 11E is a bottom view of the drill guide of FIG. 11A;

FIG. 30A is a bottom view of the clamping ring of FIG. 28 and the anterior side of a patella clamped within the clamping ring; FIG. 30B is a superior view of the clamping ring and patella of FIG. 30A;

FIG. 31A is a perspective view of a patient specific clamping ring with resection guide slots; FIG. 31B is an inferior view of the clamping ring of FIG. 31A;

DETAILED DESCRIPTION OF THE PREFERRED EMBODIMENTS

Figure 1A:
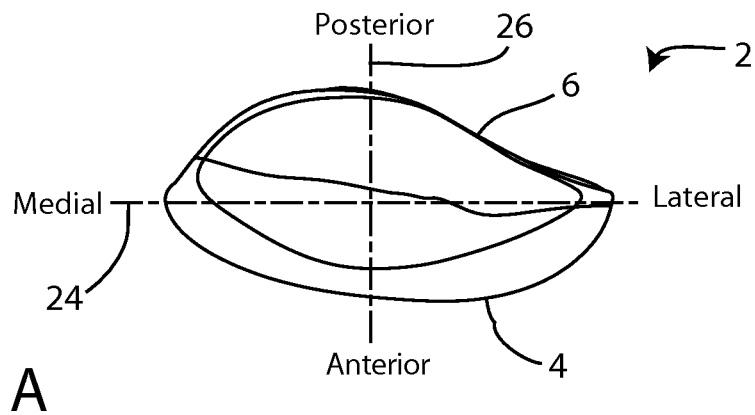
FIG. 1A is an inferior view of a natural patella.

The present disclosure relates to patellar implants and instrumentation and methods for preparation and implantation of these devices. Those of skill in the art will recognize that the following description is merely illustrative of the principles of the disclosure, which may be applied in various ways to provide many different alternative embodiments. This description is made for the purpose of illustrating the general principles of this invention and is not meant to limit the inventive concepts in the appended claims. While the present disclosure is made in the context of total knee arthroplasty for the purposes of illustrating the concepts of the design, it is contemplated that the present design and/or variations thereof may be suited to applications outside the field of total knee arthroplasty. For example, the present design and/or variations thereof may be suited to applications in knee hemiarthroplasty, patellar resurfacing alone, ankle arthroplasty, or other surgical arts.

The present disclosure relates to prosthetic patellar implants intended to replace the articulating surface of the posterior portion of the patella during a total knee arthroplasty procedure. The prosthetic patella may have an anatomic asymmetric footprint with a medialized apical surface. The anatomic geometry of the disclosed patella prostheses may cover a greater portion of the resurfaced patella in order to minimize the incidence of soft tissue ingrowth. The devices and techniques described within illustrate several concepts for achieving a strong geometric interface between the patellar implant and the resurfaced bone, minimizing the amount of bone removal required and creating anatomic coverage of the posterior patellar surface with repeatable results. The described implants contain multiple anterior features to better withstand shear loading forces at the implant-bone mating interface, which may improve the implant's resistance to loosening and migration.

The disclosed embodiments seek to improve the art and remedy the weaknesses not addressed by present devices. The disclosed method of patella preparation and implant design will allow a person skilled in the art to: remove all arthritic pathology at the articulating surface, maximize the amount of patellar bone preserved, minimize the area of uncovered resurfaced patellar bone, and maximize the implant to bone surface retention strength. Another key feature of the method and implant design is its inability to be installed in an incorrect manner. Often times if the implant site is obscured by bone cement the surgeon may be unsure of the proper implant orientation. By using differently sized medial and lateral reamers, for one example, only one possible configuration for implant installation will exist. This ensures that the implant setting procedure is self-aligning, reducing the amount of clinical error, time and surgeon frustration.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

According to an aspect of the disclosure, a system for preparing a patient's patella to receive an implant includes a clamp ring for receiving and independently immobilizing the patella, the clamp ring including: an annular ring body extending between a first edge and a second edge opposite the first edge, the ring body circumscribing an unobstructed opening extending between the first edge and the second edge; wherein at least one dimension of the clamp ring is determined by measurements specific to the patient.

Embodiments of this aspect of the disclosure may include one or more of the following features: The clamp ring further includes an attachment feature for attaching the clamp ring to a patellar preparation instrument. The attachment feature protrudes from one of the first and second edges. The clamp ring comprises an inner clamping surface for facing and contacting the patella, the inner clamping surface extending between the first edge and the second edge around the interior of the ring body. The shape of the inner clamping surface is irregular, and is determined by measurements specific to the patient. The shape of the ring body, viewed normal to the second edge, is circular. The shape of the ring body is non-circular. The first and second edges undulate. The clamp ring further comprises a straight slot extending through a portion of the ring body, the straight slot positioned for guiding a resection saw blade.

In an embodiment of this aspect of the disclosure, the system further includes a reamer guide having a guiding structure for guiding a reamer; wherein the clamp ring is rigidly coupled to the reamer guide, to permit precise reaming of the patella with the reamer.

In an embodiment of this aspect of the disclosure, the system further includes a resection guide having a guiding structure for guiding a blade; wherein the clamp ring is rigidly coupled to the resection guide, to permit precise resectioning of the patella with the blade.

In another aspect of the disclosure, a system for preparing a patient's patella to receive an implant includes: a retaining member for holding the patella in a fixed orientation, the retaining member including: a continuous strip forming a closed loop, the closed loop having an upper edge and a lower edge, the closed loop defining an open window extending between the upper edge and the lower edges; wherein at least one dimension of the retaining member is determined by measurements specific to the patient.

Embodiments of this aspect of the disclosure may include one or more of the following features: The retaining member further comprises at least one attachment feature for attaching the retaining member to a patellar preparation instrument in a fixed orientation relative to the instrument. The attachment feature protrudes from the upper edge of the closed loop. The retaining member comprises a retaining surface for facing and contacting the patella, the retaining surface extending between the upper edge and the lower edge around the interior of the closed loop. The shape of the retaining surface is irregular, and is determined by measurements specific to the patient.

In another aspect of the disclosure, a method for preparing a patient's patella to receive an implant includes: inserting the patella into a clamp, the clamp comprising an annular ring body extending between an first edge and a second edge opposite the first edge, the ring body circumscribing an unobstructed opening extending between the first edge and the second edge, wherein at least one dimension of the clamp ring is determined by measurements specific to the patient; positioning the patella in the unobstructed opening; clamping the outer periphery of the patella with the annular ring body; holding the patella in a fixed orientation relative to the annular ring body; and modifying a portion of the patella to prepare the patella to receive an implant.

Embodiments of this aspect of the disclosure may include one or more of the following features and methods: The clamp ring circumferentially contacts the patella and soft tissues immediately superior and inferior to the patella, the clamp ring suppressing the soft tissues between the patella and the clamp ring. Rigidly attaching the clamp to a patellar preparation instrument; and holding the patella in a fixed orientation relative to the patellar preparation instrument. Reaming or resecting the posterior articular surface of the patella.

In another aspect of the disclosure, a system for preparing a bone includes a first guide, the first guide including: a first collet, the first collet having a proximal end and a distal end, a first bore extending therethrough, the first bore centered about a first axis; a second collet, the second collet having a proximal end and a distal end and a second bore extending therethrough, the second bore radially centered about a second axis, wherein the first and second axes diverge from one another at an angle and the first and second bores partially overlap one another.

Embodiments of this aspect of the disclosure may include one or more of the following features: The first bore defines a first cylindrical envelope and the second bore defines a second cylindrical envelope, wherein the first and second cylindrical envelopes partially overlap one another. The radial diameters of the first and second bores are equal. The radial diameters of the first and second bores are unequal. The first and second collets share a common distal end. The proximal ends of the first and second collets are separated from one another. The first bore is partially defined by a semicircular first wall extending between the proximal end and the distal end of the first collet, and the second bore is partially defined by a semicircular second wall extending between the proximal end and the distal end of the second collet. At least one of the first and second walls has a window extending through the wall and in communication with the respective bore. A connecting bridge is formed between the first and second collets. The first wall is shaped to receive and guide a bone preparation instrument through the first bore along the first axis, and the second wall is shaped to receive and guide a bone preparation instrument through the second bore along the second axis. A clamping apparatus having a first clamp, a second clamp carried on the first guide, wherein the first guide is attached to the clamping apparatus, and the clamping apparatus is actuable to increase and decrease a distance between the first clamp and the second clamp.

In an embodiment, the angle is between about 200 and about 60°. The angle may be between about 300 and about 500. The angle may be 40°.

In an embodiment, the system includes a second guide having a third bore, wherein the second guide is carried by the first guide, the second guide shaped to guide a bone preparation instrument through the third bore. The third bore may be radially centered about a third axis. The third axis may be non-parallel with the first axis and the second axis.

In an embodiment, the second guide is receivable in one of the first and second collets, the collet having a first engagement feature which cooperates with the second guide to secure the second guide within the collet in a selected orientation. The second guide may have a second engagement feature, wherein the first and second engagement features include a track and a rail slidably receivable in the track along a straight path.

In another aspect of the disclosure, a method for preparing includes positioning a first guide adjacent the bone, the first guide including: a first collet, the first collet having a proximal end and a distal end, and a first bore extending therethrough, the first bore radially centered about a first axis; a second collet, the second collet having a proximal end and a distal end, and a second bore extending therethrough, the second bore radially centered about a second axis, wherein the first and second axes diverge from one another at an angle and the first and second bores partially overlap one another.

Embodiments of this aspect of the disclosure may include one or more of the following features and steps: The first and second collets share a common distal end. The proximal ends of the first and second collets are separated from one another. The first bore is partially defined by a semicircular first wall extending between the proximal end and the distal end of the first collet, and the second bore is partially defined a by a semicircular second wall extending between the proximal end and the distal end of the second collet. Inserting a bone preparation instrument into the first bore, the first collet guiding the bone preparation instrument along the first axis toward the bone. Inserting a bone preparation instrument into the second bore, the second collet guiding the bone preparation instrument along the second axis toward the bone. A clamping apparatus having a first clamp, wherein positioning the first guide adjacent the bone further includes clamping the bone between the first clamp and the first guide.

In an embodiment, the angle is between about 200 and about 60°. The angle may be between about 300 and about 50°. The angle may be 40°.

Embodiments of the second aspect may include one or more of the following features or steps: Attaching a second guide to the first guide, the second guide having a third bore radially centered about a third axis. The third axis may be non-parallel with the first axis and the second axis. Attaching the second guide to the first guide further includes inserting the second guide into engagement within one of the first and second collets. Inserting the second guide into engagement within one of the first and second collets further comprises sliding a first engagement feature on the collet along a straight path into engagement with a second engagement feature on the second guide to secure the second guide within the collet in a fixed orientation. Inserting a bone preparation instrument into the third bore, the second guide guiding the bone preparation instrument along the third axis toward the bone.

Figure 1B:
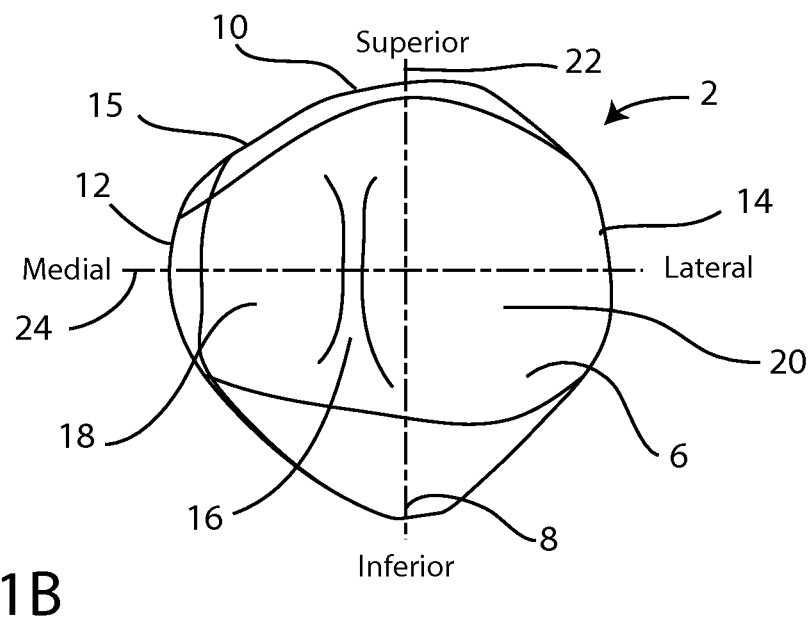
FIG. 1B is a posterior view of the patella of FIG. 1A.
Figure 1C:
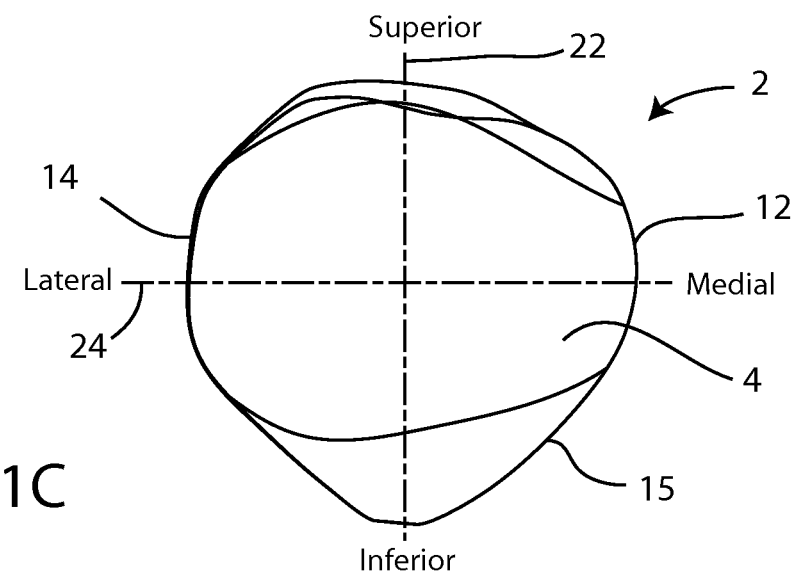
FIG. 1C is an anterior view of the patella of FIG. 1A.

Referring to FIGS. 1A-IC, views of a stylized example of a right patella, or kneecap, are shown. FIG. 1A is an inferior view of the patella, FIG. 1B is a posterior view, and FIG. 1C is an anterior view. Patella 2 has a dorsal or anterior side 4, a posterior side 6, an apex 8, a base 10, a medial border 12 and a lateral border 14. The anterior surface connects to the quadriceps femoris muscles, and the posterior surface articulates with the patellar surface of the condyles of the femur. On the posterior side 6, a vertical ridge 16 extends generally superior-inferiorly across the patella, dividing the posterior surface into a medial facet 18 and a lateral facet 20. The patella may be characterized as having a superior-inferior axis 22, a medial-lateral axis 24, and an anterior-posterior axis 26. The vertical ridge 16 is medialized, meaning is it offset toward the medial side from the superior-inferior 22 axis of the patella. The vertical ridge 16 may also be referred to as a medial ridge. The patella has an outer periphery 15, which is the outermost edge of the patella when viewed from the posterior or anterior view.

Referring to FIGS. 2A-2F, one embodiment of a patellar prosthesis, or implant, of the present disclosure is shown. Patellar implant 100, which may be referred to as a bi-planar implant, includes an anterior side 102 having an anterior attachment surface 104, which may be a bone-contacting surface. Generally opposite the anterior side 102 is a posterior side 106 having a posterior articulation surface 108. In the embodiment shown, the posterior articulation surface includes a medial articulation surface 118 and a lateral articulation surface 120. A dome 116, which may spherical, includes a portion of both surfaces 118, 120 and may be medialized, or offset toward the medial articulation surface 118 from the sagittal centerline of the implant. It is appreciated that in this and other embodiments of the patellar implants disclosed within, the posterior articulation surface may include other shapes which may be rounded, convex, faceted, complexly curved, domed, saddle-shaped, sombrero-shaped, stepped, radially symmetrical, bilaterally symmetrical, asymmetrical, irregular, or any other shape known in the art capable of articulating with natural or prosthetic femoral condyles.

Figure 2A:
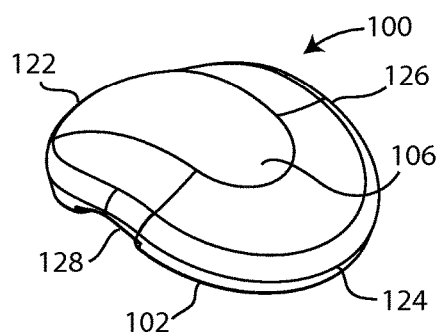
FIG. 2A is an isometric posterior view of a bi-planar prosthetic patellar implant.
Figure 2B:
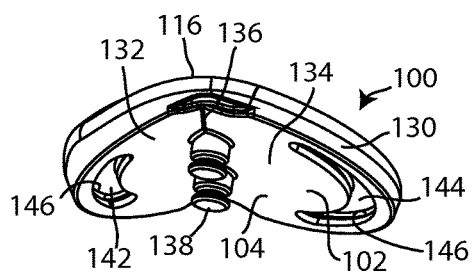
FIG. 2B is an anterior perspective view of the patellar implant of FIG. 2A.
Figure 2C:
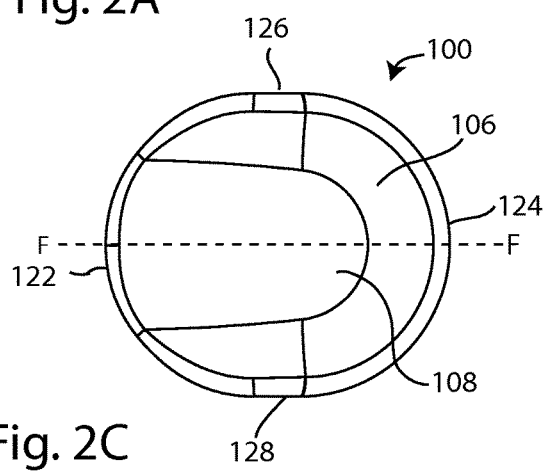
FIG. 2C is a posterior view of the patellar prosthesis of FIG. 2A.
Figure 2D:
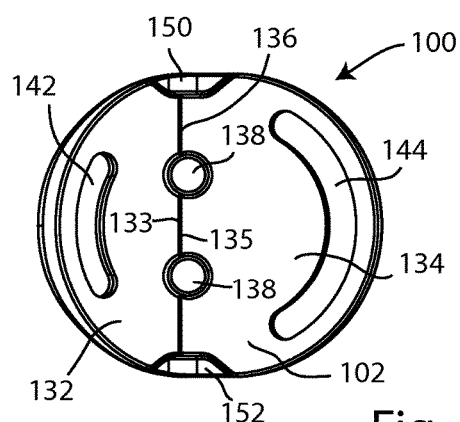
FIG. 2D is an anterior view of the patellar implant of FIG. 2A.
Figure 2E:
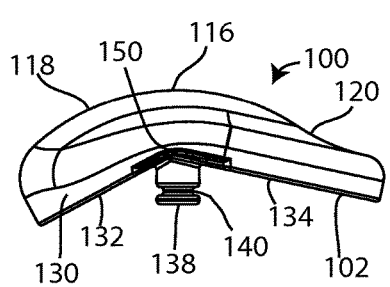
FIG. 2E is a superior view of the patellar implant of FIG. 2A.
Figure 2F:
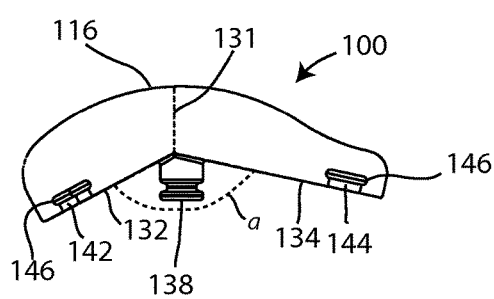
FIG. 2F is a superior cross-sectional view of the patellar implant of FIG. 2A taken along section line F-F in FIG. 2C.

The implant 100 further includes a medial end 122, a lateral end 124, a first end 126, and a second end 128. The embodiment shown in FIGS. 2A-2F is bilaterally symmetrical, meaning in this instance that a division of the implant medially-laterally along the transverse plane will result in two mirror-image halves. It is appreciated that implant 100 may be implanted as a right or left patella by rotating the implant to the proper orientation. In FIGS. 2A and 2C, the implant 100 is shown as a right patellar implant because first end 126 is shown on the superior side and second end 128 is shown on the inferior side. In a left implant, the first and second ends would be reversed, i.e. first end 126 would be inferior and second end 128 would be superior. A perimeter 130 circumscribes the outer edge of the implant 100 adjacent the anterior side 102. The shape of the implant as seen from the anterior and posterior views shown in FIGS. 2C and 2D is oval; an oval or ovoid implant provides better coverage of a resected patella than a circular implant and may reduce the incidence of patellar crepitus. A thickness or anterior-posterior height of implant 100 may be measured between the anterior and posterior surfaces, and is typically measured normal to the tangent of dome 116, as shown by dashed line 131. The implant 100 may be manufactured in a variety of sizes in which the medial-lateral, inferior-superior and/or anterior-posterior dimensions may vary. For example, the ratio of medial-lateral to inferior-superior dimension may range between about 1.17 and about 1.27.

The anterior side 102 is shaped for attachment to a resected posterior surface of a patella. The anterior attachment surface 104 can be described as bi-planar, and includes a medial attachment surface 132 and a lateral attachment surface 134. Attachment surfaces 132, 134 are substantially planar, defining first and second planes, respectively. In the embodiment shown, first and second planes are not co-planar, but other embodiments may include co-planar medial and lateral attachment surfaces. Medial attachment surface 132 terminates laterally at a lateral bounding edge 133. Lateral attachment surface 134 terminates medially at a medial bounding edge 135. In the embodiment shown the anterior attachment surface 104 is peaked; the medial and lateral attachment surfaces are angled relative to one another and their bounding edges 133, 135 converge at a common interior corner, or intersection 136. Intersection 136, which lies along a straight line intersecting with the perimeter 130 at the first and second ends 126, 128 of the implant, extends generally superior-inferiorly on the opposite side of the implant from, and centered on, the dome 116. The planar medial and lateral attachment surfaces 132, 134 form an angle a between them. Angle a may match the angle between the medial and lateral facets of a native patella. In some embodiments, angle a is between about 90° and about 180°. In some embodiments, angle a is between about 120° and about 150°. In some embodiments, angle a is about 130° plus or minus 10°. In some embodiments, angle a is 140°.

In other embodiments, the intersection or peak of the anterior attachment surface may be offset from the dome 116, or highest point of the posterior articulation surface. The lateral attachment surface of patellar implants disclosed herein may be wider than the medial attachment surface; in the embodiment shown, lateral attachment surface 134 is 25% wider, measured medial-laterally, than the medial attachment surface 132. In some embodiments, such as of FIG. 2D, the inferior-superior dimension of each of the medial and lateral attachment surfaces, measured mid-facet, may be approximately equal to one another; in other embodiments they may be unequal.

One or more posts, or pegs 138 project anteriorly from the anterior attachment surface 104. Pegs 138 may be cylindrical and include one or more grooves 140 which help to retain the implant when used with bone cement for attachment to the patella. The cement will flow into the groove, creating a cement mantle to permanently lock in place the implant. Other shapes for pegs 138 and for other embodiments disclosed herein are contemplated, including square, hexagonal, pentagonal, toothed, or irregular. In some embodiments, the number and distribution of pegs 138 may vary. In some embodiments the peg 138 locations are consistent throughout a range of implant sizes upsizing and downsizing options from smallest to largest size. The pegs 138 shown on implant 100 are medialized, where they may be implanted into the thickest, healthiest remaining bone along the ridge 16 of the patella. This may provide a more secure attachment than pegs placed where they would be implanted more toward the medial and/or lateral borders of the patella, into thinner bone. The inclusion of more than one peg provides additional lateral and rotational stability compared to a single peg design.

The anterior attachment surface 104 further includes a medial recess 142 and lateral recess 144, which are formed as curved indentations undercut into the anterior side 102. The curved shapes of the recesses may match the outer curvature of the implant. The recesses 142, 144 may include grooves 146 which may provide increased surface area to improve cement fixation of the implant to the patella. The recesses 142, 144 are placed near the outer perimeter 130 of the implant and farther away from the center of the implant, to provide increased resistance to loading. Other embodiments of the patellar implant may vary in the number, shape and/or distribution of any recesses, or may include no recesses.

Patellar implant 100 further includes a superior or first pocket 150 and an inferior or second pocket 152. Each pocket is formed along a portion of the intersection of the perimeter 130 and the anterior attachment surface 104, and forms a recess into the anterior attachment surface. Each pocket may straddle, or cross, the intersection 136. The inclusion of pockets 150, 152 may allow retention of more patellar bone at the area of the medial ridge than if the recessed pockets were not present. Additionally, the pockets allow the implant to be fit without additional surface clean-up steps such as rongeuring the residual native bone volume away.

Figure 3A:
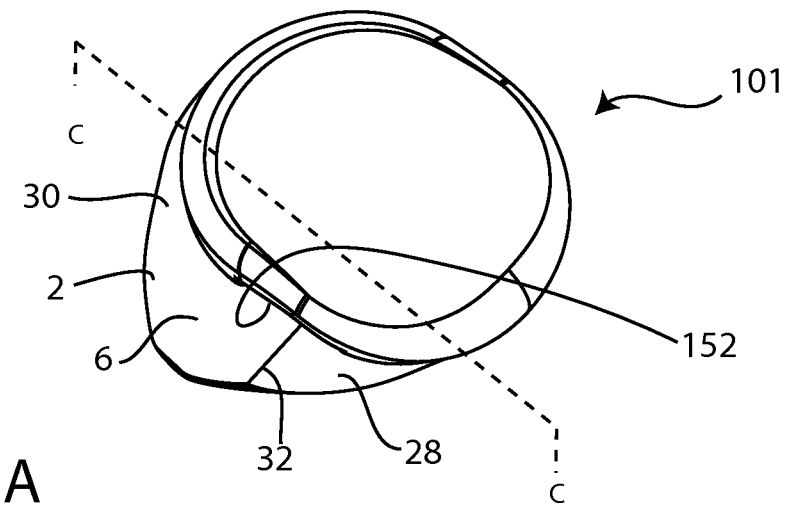
FIG. 3A is an isometric view of a bi-planar prosthetic patellar implant attached to a prepared patella.
Figure 3B:
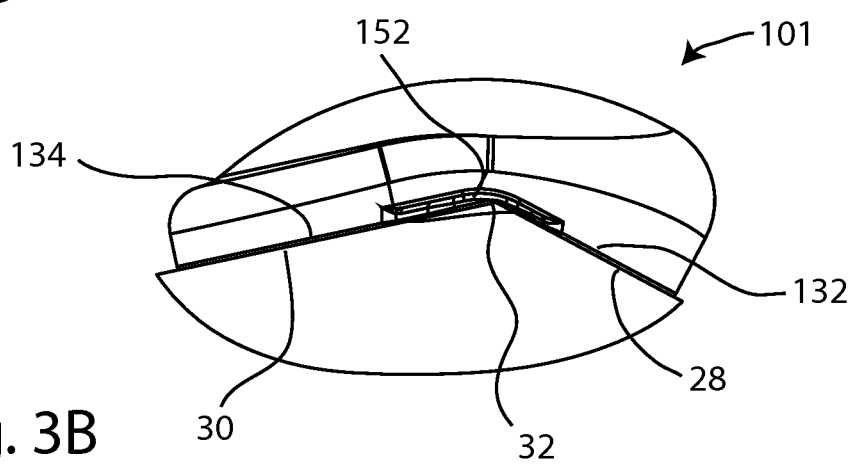
FIG. 3B is an inferior view of the implant and patella of FIG. 3A.
Figure 3C:
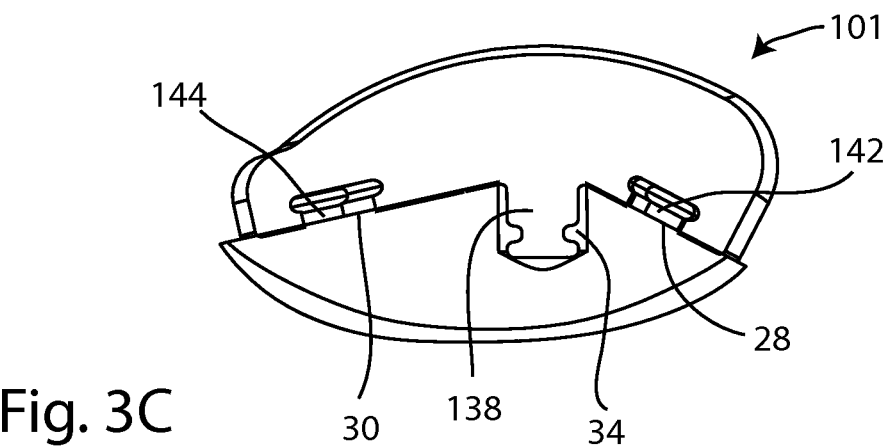
FIG. 3C is a cross-sectional inferior view of the implant and patella of FIG. 3A taken along line C-C of FIG. 3A.

FIGS. 3A through 3C show a patellar implant 101 implanted on to a prepared patella 2. Implant 101 may have many of the same features as implant 100, only differing in relative size, and shape of the posterior articulation surface. The posterior side 6 of patella 2 has been reamed or resected to include prepared medial facet 28 and prepared lateral facet 30, divided by a prepared medial ridge 32. The medial attachment surface 132 is immediately adjacent, parallel to, and flatly abutting the prepared medial facet 28, and the lateral attachment surface 134 is immediately adjacent, parallel to, and flatly abutting the prepared lateral facet 30. Peg 138 is received in a peg hole 34. Recesses 142, 144 are adjacent to and in communication with the prepared medial and lateral facets 28 and 30, respectively. Although not visible, a cement mantle may attach the implant to the prepared surfaces, and occupy the recesses 142, 144 and any space between the peg 138 and surfaces of the peg hole 34. Pocket 152 bridges over ridge 32, allowing retention of additional patellar bone.

Figure 4A:
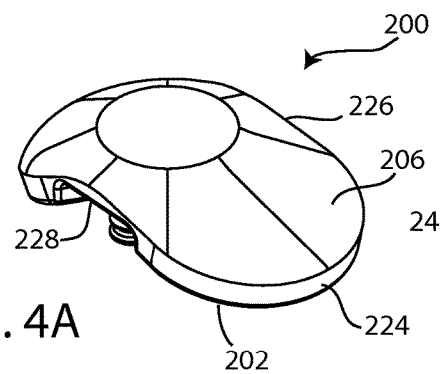
FIG. 4A is an isometric posterior view of a prosthetic patellar implant having two convex anterior attachment surfaces.
Figure 4B:
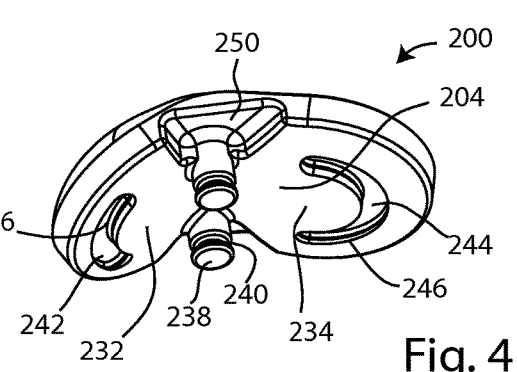
FIG. 4B is an anterior perspective view of the patellar implant of FIG. 4A.
Figure 4C:
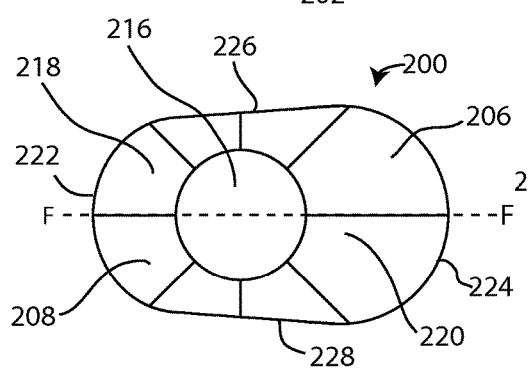
FIG. 4C is a posterior view of the patellar implant of FIG. 4A.
Figure 4D:
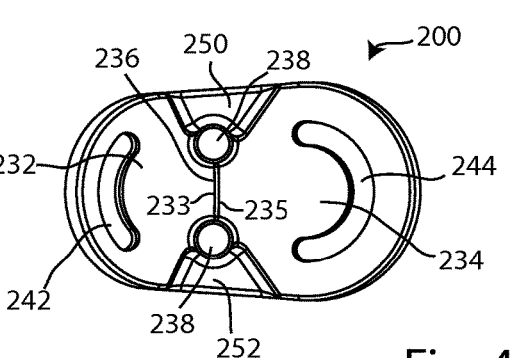
FIG. 4D is an anterior view of the patellar implant of FIG. 4A.

Referring to FIGS. 4A through 4F, an alternative embodiment of a patellar implant which may be referred to as tri-convex implant is shown. Patellar implant 200 includes an anterior side 202 having an anterior attachment surface 204, which may be a bone-contacting surface. Generally opposite the anterior side 202 is a posterior side 206 having a posterior articulation surface 208. In the embodiment shown, the posterior articulation surface 208 includes a medial articulation surface 218 and a lateral articulation surface 220. A dome 216, which may be spherical, includes a portion of both surfaces 218, 220 and may be medialized, or offset toward the medial articulation surface 218 from the sagittal centerline of the implant. The implant 200 further includes a medial end 222, a lateral end 224, a first end 226, and a second end 228. The embodiment shown in FIGS. 4A-4F is bilaterally symmetrical, meaning in this instance that a division of the implant medially-laterally along the transverse plane will result in two mirror-image halves. It is appreciated that implant 200 may be implanted as a right or left patella by rotating the implant to the proper orientation. In FIGS. 4A and 4C, the implant 200 is shown as a right patellar implant because first end 226 is shown on the superior side and second end 228 is shown on the inferior side. In a left implant, the first and second ends would be reversed, i.e. first end 226 would be inferior and second end 228 would be superior. A perimeter 230 circumscribes the outer edge of the implant 200 adjacent the anterior side 202. The shape of the implant as seen from the anterior and posterior views shown in FIGS. 4C and 4D may be described as ovoid. A thickness or height of implant 200 may be measured between the anterior and posterior surfaces, and is typically measured normal to the tangent of dome 216, as shown by dashed line 231. The implant 200 may be manufactured in a variety of sizes in which the medial-lateral, inferior-superior and/or anterior-posterior dimensions may vary.

One or more pegs 238 project anteriorly from the anterior attachment surface 204. Pegs 238 may be cylindrical and include one or more grooves 240 which help to retain the implant when used with bone cement for attachment to the patella. The number and distribution of pegs 238 may vary. The pegs 238 shown on implant 200 may be medialized, so they can be implanted into the thickest, healthiest remaining bone along the ridge 16 of the patella.

The anterior side 202 is shaped for attachment to a resected posterior surface of a patella. The anterior attachment surface 204 includes a medial attachment surface 232 and a lateral attachment surface 234. Medial attachment surface 232 terminates laterally at a lateral bounding edge 233. Lateral attachment surface 234 terminates medially at a medial bounding edge 235. In the embodiment shown the anterior attachment surface 204 is peaked; the medial and lateral attachment surfaces are angled relative to one another and their bounding edges 233, 235 converge at a common interior corner, or intersection 236. Intersection 236 lies along a straight line generally superior-inferiorly on the opposite side of the implant from, and centered relative to dome 216. The inferior-superior dimension of each of the medial and lateral attachment surfaces 232, 234, measured mid-facet, are unequal, as the lateral attachment surface 234 is taller than the medial attachment surface 232. In other embodiments, the medial and lateral attachment surfaces may be equal in surface area.

Figure 4E:
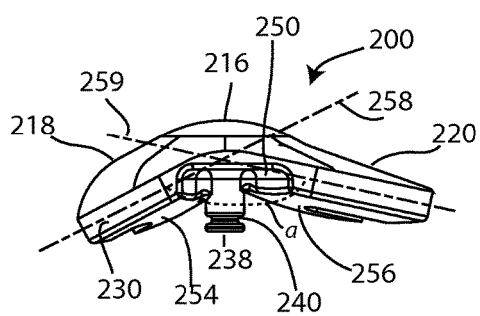
FIG. 4E is a superior view of the patellar implant of FIG. 4A.
Figure 4F:
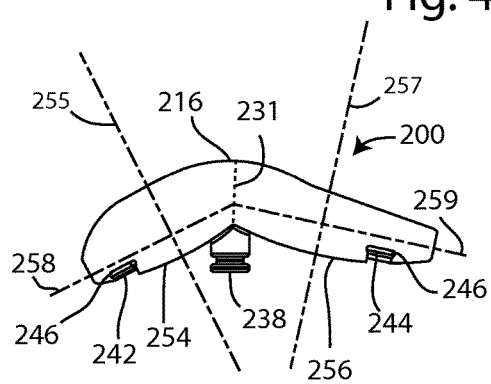
FIG. 4F is a superior cross-sectional view of the patellar implant of FIG. 4A taken along section line F-F in FIG. 4C.

Referring to FIG. 4E, the medial and lateral portions of the implant 200 are angled relative to one another. Dashed line 258 in FIG. 4E represent a plane along which the medial portion is aligned, and dashed line 259 represents a plane along which the lateral portion is aligned. The planes 258, 259 are angled relative to one another at an angle a, which can have the same values as disclosed for angle a of patellar implant 100. The anterior attachment surface 204 includes a medial convexity 254 protruding from the medial attachment surface and a lateral convexity 256 protruding from the lateral attachment surface, seen in profile in FIGS. 4E and 4F. Each convexity may be formed radially about an axis 255, 257 normal to its respective attachment surface and normal to the respective medial and lateral planes 258, 259. The medial and lateral convexities 254, 256 may be contoured to complementarily match concavities reamed into the prepared patellar surfaces, and may provide additional resistance to shearing forces. The shape of each individual convexity 254 or 256 may be radially symmetrical, for example a dome shape, or in other embodiments may be asymmetrical. The thickness or height of each convexity may vary according to implant size or patient determined factors.

The anterior attachment surface 204 further includes a medial recess 242 and lateral recess 244, which are formed as curved indentations undercut into the anterior side 202, and may be formed on the medial and lateral convexities 254, 256. The curved shapes of the recesses may match the outer curvature of the implant. The recesses 242, 244 may include grooves 246 which may provide increased surface area to improve cement fixation of the implant to the patella.

Patellar implant 200 further includes a superior or first pocket 250 and an inferior or second pocket 252. Each pocket is formed along a portion of the intersection of the perimeter 230 and the anterior attachment surface 204, and forms a recess into the anterior attachment surface. Each pocket may cross the intersection 236 or an axis coaxial with the intersection 236. The inclusion of pockets 250, 252 may allow retention of more patellar bone at the area of the medial ridge than if the recessed pockets were not present.

The patellar implants disclosed herein can be formed of a single solid construction, for example formed from a block of UHMWPE (ultra-high molecular weight polyethylene). Alternately, an implant may be of a composite porous metal and UHMWPE construction. It is appreciated that other embodiments of the implants disclosed herein include the use of alternative materials including but not limited to, PEEK, titanium and titanium alloys, Nitinol, cobalt chrome, stainless steel, ceramics, polyethylene, cross-linked polyethylene, UHMWPE, and biocompatible materials, among others. They may also encompass a variety of surface treatments to encourage bony attachment such as porous coatings, hydroxyapatite, and TCP, among others. Any implant disclosed herein may include a radiographic marker for imaging purposes.

FIGS. 5 through 12 show instruments and steps for preparation of a patella for implantation of a patellar implant. It is appreciated that the instruments and methods disclosed herein may be used with the patellar implants of this disclosure including implants 100 or 200, or may used with other patellar implants. FIGS. 5 through 12 show a reaming assembly and associated instrumentation which may be used to ream a patella for implantation of a patellar implant with convex attachment surfaces, for example patellar implant 200. However, it is appreciated that the methods disclosed with reference to FIGS. 5 through 12 could be modified for implantation of a patellar implant with planar attachment surfaces. FIGS. 13 through 20B show a resection assembly and associated instrumentation which may be used to ream a patella for implantation of a patellar implant with bi-planar attachment surfaces, for example patellar implant 100. However, it is appreciated that the methods disclosed with reference to FIGS. 13 through 20B could be modified for implantation of a patellar implant with convex or concave attachment surfaces.

Figure 5:
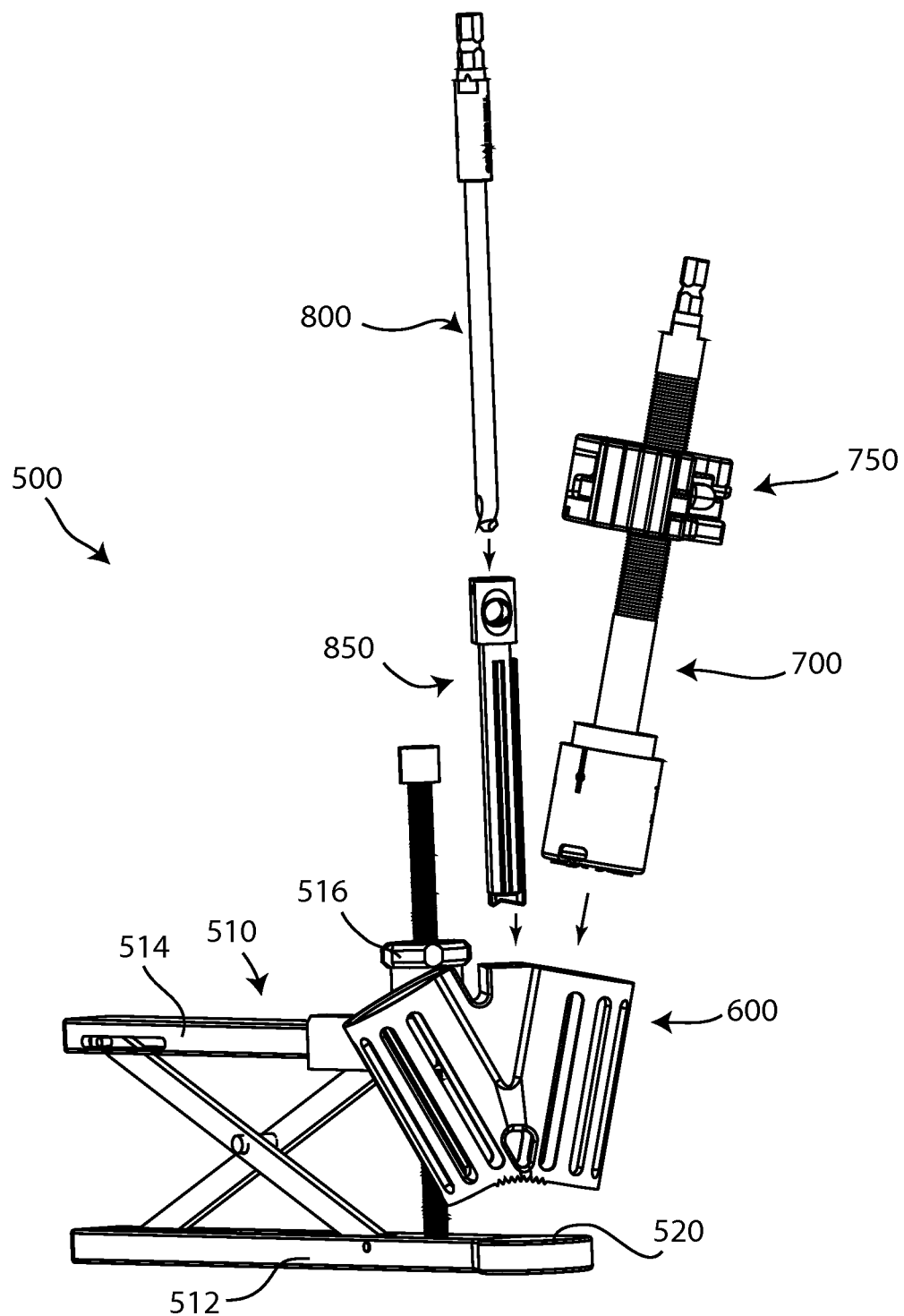
FIG. 5 is a partially exploded view of a reaming assembly including a modular clamping apparatus, a reamer, a depth gauge assembly, a drill, a drill guide, and a dual axis reaming guide.
Figures 6A, 6B:
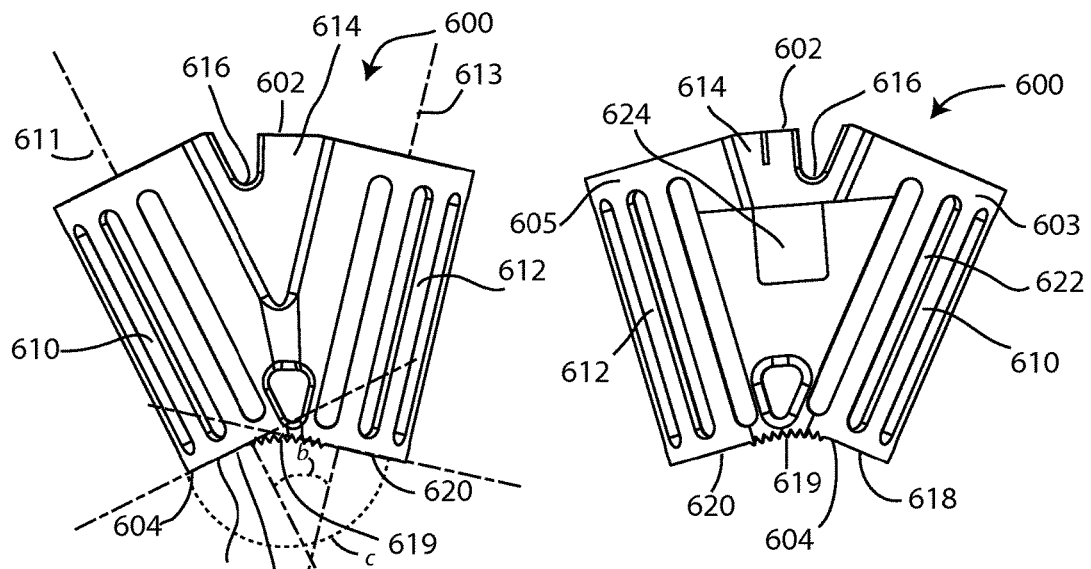
FIG. 6A is a side view of the dual axis reaming guide of FIG. 5.
FIG. 6B is an opposite side view of the dual axis reaming guide of FIG. 6A.
Figure 6C:
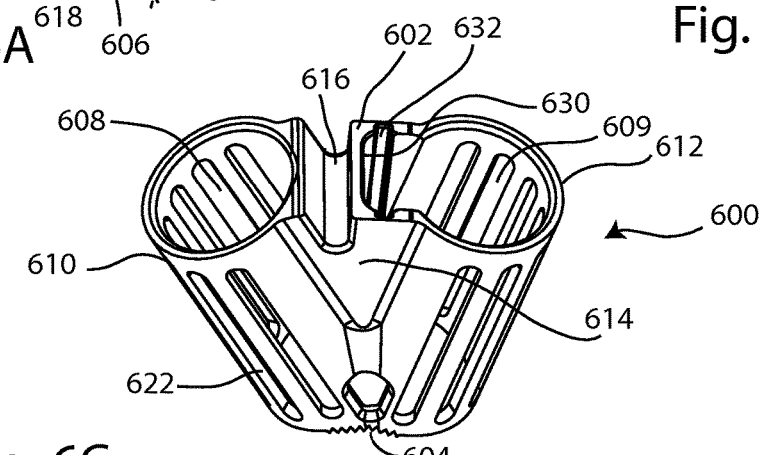
FIG. 6C is a top perspective view of the dual axis reaming guide of FIG. 6A.
Figure 6D:
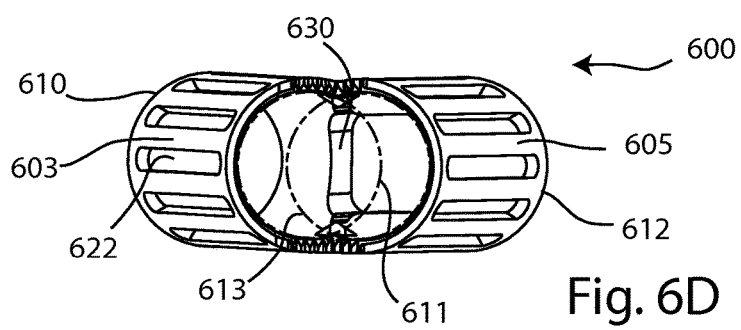
FIG. 6D is a bottom view of the dual axis reaming guide of FIG. 6A.

Referring to FIG. 5, a perspective view shows a reaming assembly 500. Reaming assembly 500 includes a modular clamping apparatus 510, on which a dual axis reaming guide 600 is mounted. In exploded form, a reamer 700 with adjustable depth gauge assembly 750 is shown, and a drill 800 with drill guide 850. Reamer 700 and drill 800 are examples of bone preparation instruments that may be used with reaming assembly 500; it is appreciated that other bone preparations instruments could also be used with the assembly, including rongeurs, punches, mills, rasps, and shavers, among others. The modular clamping apparatus includes a first clamp arm 512 connected to a second clamp arm 514 by a cross-connection. Actuation of an actuator 16, which may be a knob, can move first and second clamp arms 512, 514 toward or away from one another to clamp or release an object placed between the clamp arms. Clamping arm 512 further comprises a first clamp 520 which may be an anterior clamp. Anterior clamp 520 may have a concave surface for receiving a convex anterior surface of a patella. One or more posts or pegs 522 may be present on the anterior clamp 520 which may assist in restraining the patella.

The dual axis reaming guide 600 is shown in several views in FIGS. 6A-6D. Reaming guide 600 includes a first or proximal end 602, and a second or distal end 604 which may function as a second, or posterior reaming clamp 606 when the guide 600 is operatively attached to the modular clamping apparatus. Posterior reaming clamp 606 may include teeth, spikes, serrations or other features to assist in gripping a patella. Reaming guide 600 further includes a first or medial collet 610 having a first bore 608 centered around a longitudinal first collet axis 611, and a second or lateral collet 612 having a second bore 609 centered around a longitudinal second collet axis 613. First collet axis 611 diverges from second collet axis 613 by an angle b. In one embodiment angle b is 40°. In some embodiments, angle b is between about 30° and about 50°. In some embodiments, angle b is between about 20° and about 60°. Each collet bore 608, 609 defines a cylindrical envelope from the first end 602 to the second end 604. The radial diameters of the bores 608, 609 may be equal as in FIGS. 6A-6D, or unequal in other embodiments. First collet 608 partially defined by a semicircular first wall 603 extending between the proximal end and the distal end of the first collet 610, and the second bore 609 is partially defined by a semicircular second wall 605 extending between the proximal end and the distal end of the second collet 612.

At the second end 604, the posterior reaming clamp 606 is arched as it transitions between the distal ends of the first and second collets 610, 612. The arch shape of the posterior reaming clamp 606 may closely match the contour of the posterior surface of a patella. The posterior reaming clamp may comprise a medial segment 618, a lateral segment 620, and an arch segment 619 intermediate the medial and lateral segments 618, 620. The medial and lateral segments 618, 620 may be perpendicular to their respective collet axes 611, 613, and are angled relative to each another at angle c. Angle c may be the same as angle a of the patellar implants 100, 200. For example, in one embodiment angle c is 140°. In some embodiments, angle c is between about 90° and about 180°. In some embodiments, angle c is between about 120° and about 150°. In some embodiments, angle c is about 130° plus or minus 10°.

A bridge 614, which may be triangular, spans the distance between the medial and lateral collets 610, 612 toward the proximal end 602. A V-shaped medial ridge guide 616 is formed in the bridge 614. Toward the distal ends of the collets, a cylindrical envelope defined by each collet bore may be in communication with one another and partially overlap one another, as shown by dashed line circles 611 and 613, which represent the distal ends of the medial and lateral cylindrical envelopes, respectively. At least one window 622 is formed in guide 600 to allow viewing of reaming instruments and steps. An attachment fitting which may be shaped as a slot 624 may be present on the guide 600 for releasable attachment to the modular clamping apparatus 510.

A drill guide slot 630 extends along a portion of the lateral collet 612. The drill guide slot 630 includes at least one drill guide track 632. The drill guide slot 630 and tracks 632 are shaped to co-axially accept drill guide 850.

Referring to FIGS. 6C and 8 through 10, a reamer 700 may be guided through medial and lateral collets 610, 612 to ream a posterior patellar surface in preparation for implantation of an implant. Reamer 700 includes an attachment section 702 for attachment to a powered drive, a reamer shaft 704, and a reamer head 706. Reamer shaft 704 includes a series of flanges 708 distributed along at least a portion of the shaft. The flanges 708 may take the forms of ridges formed on, or grooves or indentations incised into or through, the surface of the shaft. The reamer head 706 includes a distal cutting surface 710 with at least one cutting edge 712 formed thereon. One or more cutting windows 714 may be included on the head. The distal cutting surface may be planar to form a planar reamed surface on a reamed bone, convex to form a concave reamed surface, or concave to form a convex reamed surface. The diameter of the reamer head 706 may be the same as the diameters of the bores 608, 609.

Figure 9A:
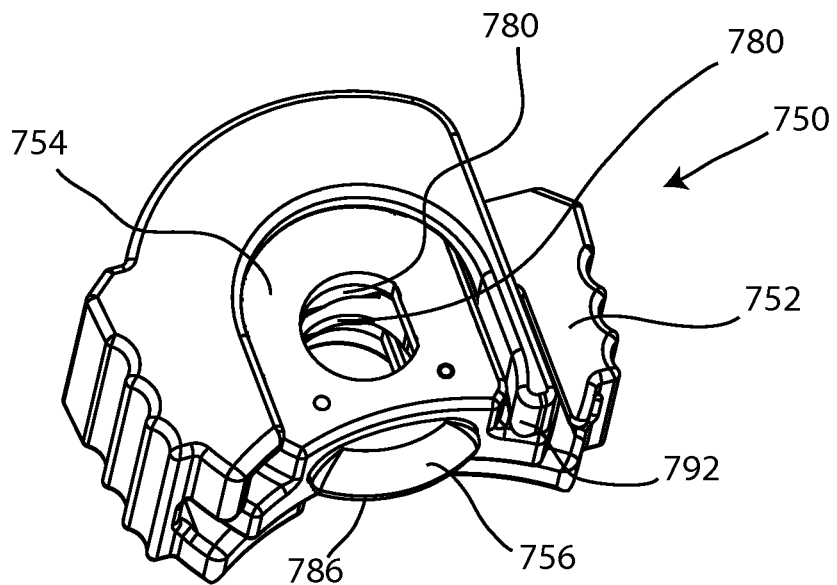
FIG. 9A is an isometric view of the depth gauge assembly of FIG. 5, the depth gauge assembly including a depth gauge and a depth stop.
Figure 9B:
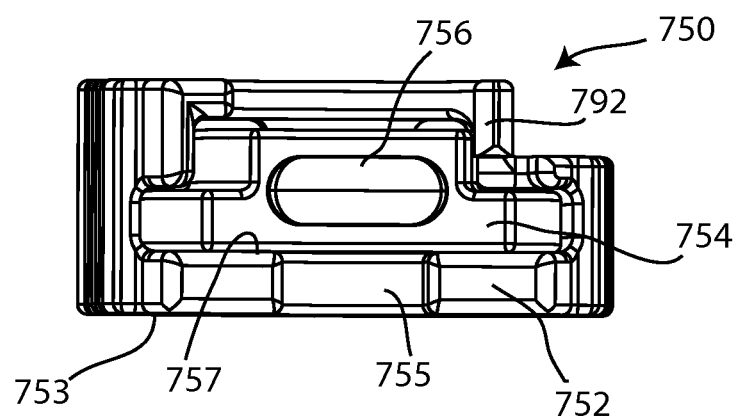
FIG. 9B is a side view of the depth gauge assembly of FIG. 9A.
Figure 10:
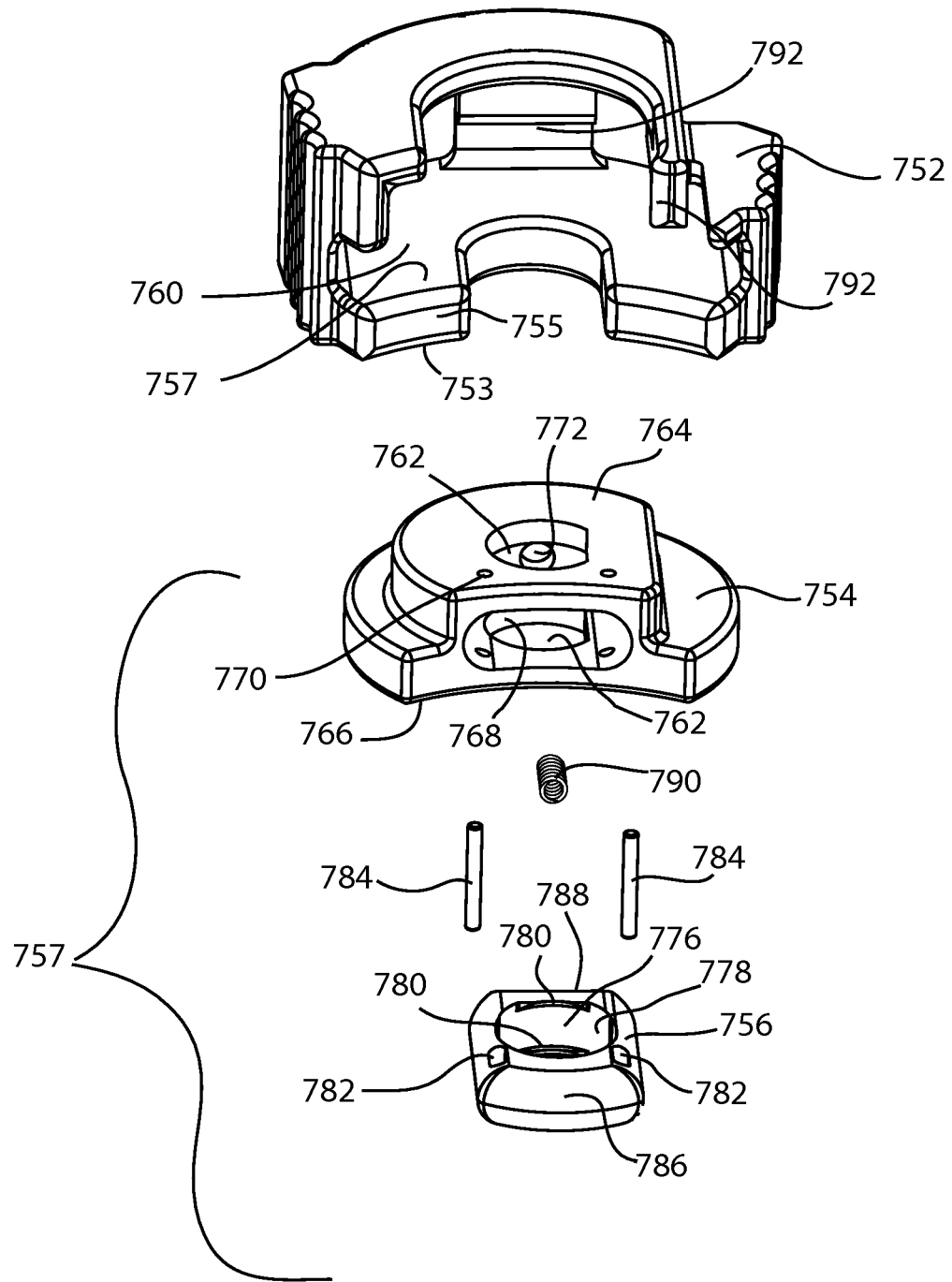
FIG. 10 is an exploded view of the depth gauge assembly of FIG. 9A.

FIGS. 9A, 9B and 10 show depth gauge assembly 750 which may be snapped onto reamer 700 to control the reaming depth as the reamer 700 is used in reaming assembly 500. Depth gauge assembly 750 may be made of plastic, and may include an outer housing 752 which may also be called a depth gauge, an inner housing 754, and a slider 756. Outer housing 752 is generally U-shaped, and includes an outer housing recess 760 shaped to receive the inner housing 754. Outer housing 752 may also include a bottom surface 753, gripping features and indicia. Inner housing 754 may be shaped as a truncated disc, and is sized and shaped to fit within the outer housing recess 760. An inner housing bore 762 extends between top 764 and bottom 766 surfaces of the inner housing 754. An inner housing recess 768 is formed in the interior of the inner housing 754 and is shaped to receive the slider 756. A plurality of pin holes 770 extend through the inner housing 754, and a blind spring hole 772 is indented in the inner housing 754, in communication with the inner housing recess 768.

The slider 756 includes a slider bore 776 extending between the top and bottom of the slider 756, the slider bore 776 circumscribed by a bore wall 778. At least one protruding step 780 is formed along a portion of the bore wall 778. The steps 780 are shaped to mesh with flanges 708 on the reamer shaft 704. A pair of elongated slots 782 extend between the top and bottom of the slider 756, to receive connecting pins 784. An actuation surface, which may be a button 786, is formed on one exterior surface of the slider 756, and a back wall 788 is opposite the actuation surface.

When the depth gauge assembly is operatively assembled as in FIGS. 5 and 9A, a spring 790 is received in the blind spring hole 772 of the inner housing 753. Slider 756 is received in inner housing recess 768, trapping the spring 790 in the blind spring hole 772 and against the slider back wall 788. Pins 784 extend through pin holes 770 and elongated slots 782. The elongated shapes of the slots 782 allow slider 756 to travel a limited distance within inner housing recess 768 when assembled with the pins. Inner housing 754 and slider 756 assembled together form a depth stop 757. The inner housing 754 and slider 756 are received in the outer housing recess 760. When the button 786 is depressed, slider bore 776 may become coaxially aligned with inner housing bore 762, and the assembly 750 may be slid on to the reamer shaft 704, with reamer shaft 704 passing through bores 776, 762. When button 786 is released, steps 780 may engage with flanges 708 on reamer shaft 704 to lock the depth gauge assembly 750 at a desired position on the reamer shaft. Alternatively, the slider 756 and inner housing 754 may be assembled together with pins 784 and spring 790 as previously described, and slid on the reamer shaft 704. Then outer housing 752 may be slid or snapped on to the inner housing 754. A tab 792 on the outer housing 752 may form a snap fit with a portion of the inner housing 754.

Referring to FIGS. 5, 7 and 11A-11F, drill 800 may be used with drill guide 850 to drill implant peg holes into a prepared patella at a desired location and depth. Drill 800 includes an attachment section 802 for attachment to a powered drive, a drill shaft 804, and a bit 806. A drill depth stop 808, which may be shaped as a collar, is formed on a portion of the drill shaft 804. The drill guide 850 is generally elongated and tubular, extending between a first drill guide end 852 which may be proximal, a second drill guide end 854 which may be distal, a medial drill guide side 856, a lateral drill guide side 858, and first and second intermediate drill guide sides 860, 862 interposed between the medial and lateral drill guide sides 856, 858. First and second drill guide rails 864, 866 are formed on the first and second drill intermediate drill guide sides 860, 862, respectively. A third drill guide rail 868 is formed on the lateral drill guide side 858. The drill guide rails are shaped to be slidingly received in the drill guide tracks 632 and slot 630 in the reaming guide 600. The inclusion of the third rail 868 and slot 630 may ensure proper positioning of the drill guide relative to the collet as the drill guide can preferably only fit in one selected orientation. In other embodiments, it is appreciated that the locations of the drill guide tracks and rails may be reversed, for example, rails may be formed on the reaming guide collet and tracks may be formed on the drill guide. Also, the tracks and rails may include dovetails or other complementary features to ensure a close guiding fit between the drill guide and the collet.

At the distal or second drill guide end 854 is an alignment surface 870 which may be asymmetrically shaped to align the drill guide on the patellar surface. The alignment surface 870 may include a medial surface portion 872 and a lateral surface portion 874 which diverge from one another to form an alignment notch 875. Toward the proximal or first drill guide end 852, a lip or shoulder 876 serves as a stop to control depth of insertion of the drill guide 850 into the reaming guide 600. A first drill guide bore 880 and a second drill guide bore 882 extend between the first and second drill guide ends 852, 854. The first and second drill guide bores 880, 882 may be slightly laterally offset relative to the alignment surface 870, as seen in FIG. 11E. This slight lateral offset may allow openings for implant pegs to be drilled into the thickest available portion of the patella. In other embodiments, only one, or multiple drill guide bores may be present.

Figure 12:
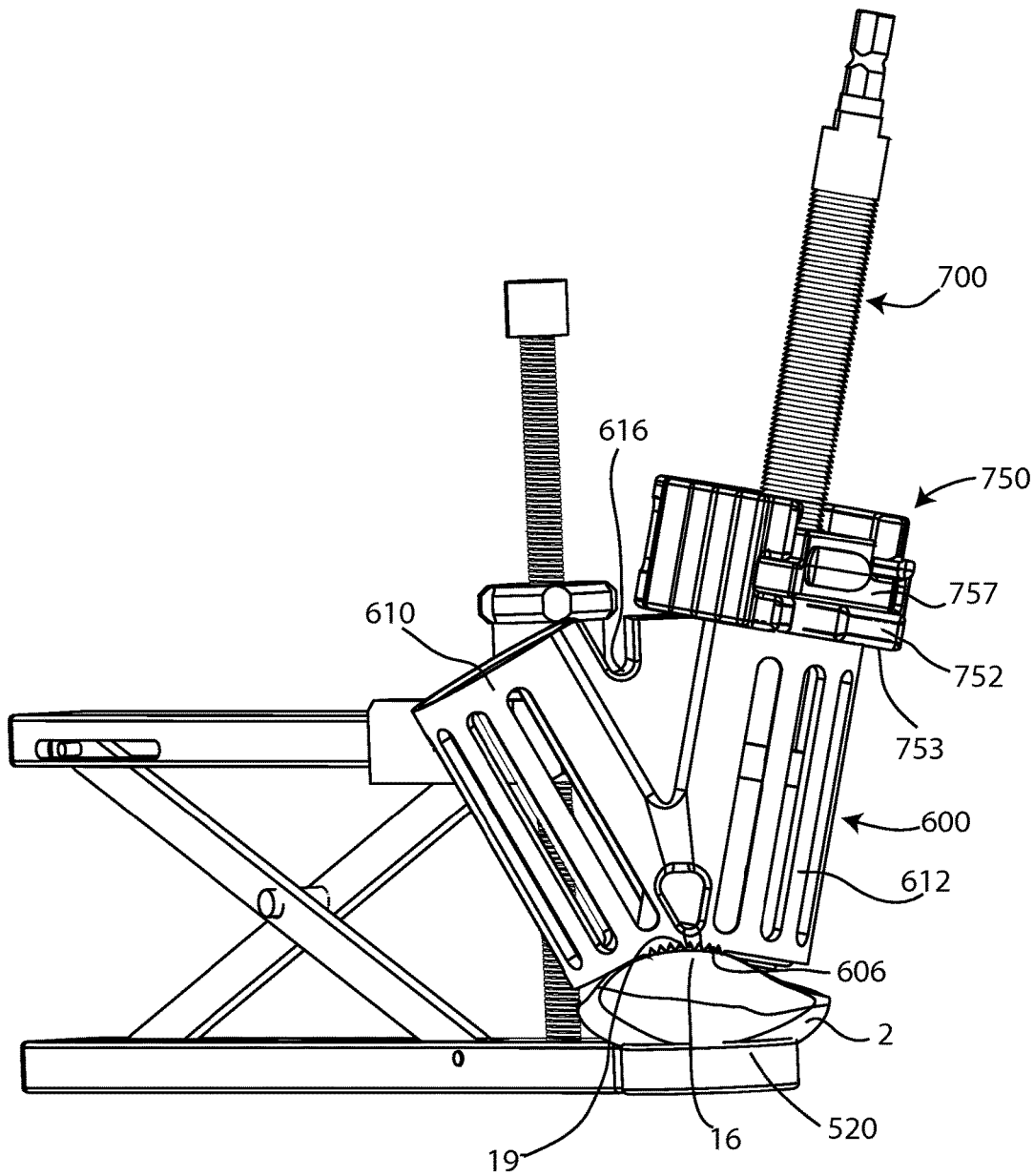
FIG. 12 is a perspective view of the modular clamping apparatus, reamer, depth gauge assembly, and dual axis reaming guide of FIG. 5 with a patella clamped between the clamping apparatus and the dual axis reaming guide and the reamer lowered into one side of the dual axis reaming guide.
Figure 22:
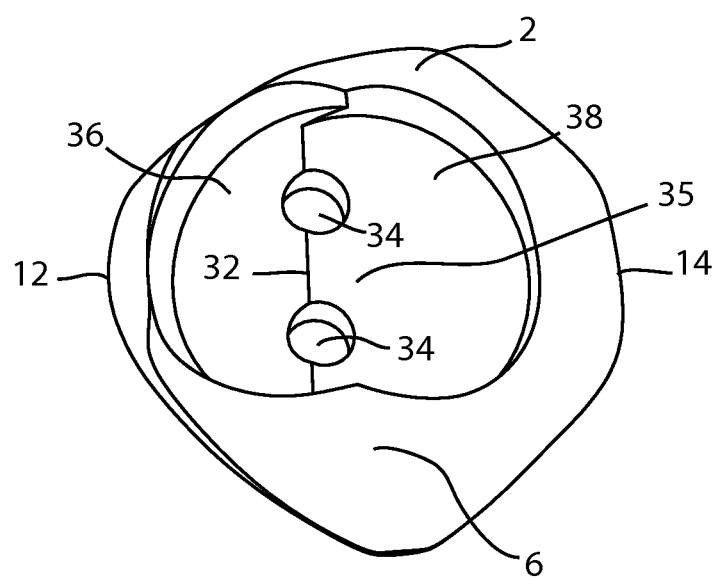
FIG. 22 is a posterior perspective view of a patella reamed and drilled according to methods disclosed herein using instrumentation shown in FIGS. 5-12.

With reference to FIGS. 5 and 12, one method of patella preparation is described. Patella 2 may be clamped between anterior clamp 520 and posterior clamp 606, with arch segment 619 spanning the medial ridge 16 of the patella and medial ridge guide 616 aligned with the medial ridge 16. Reamer 700, in a non-powered or non-reaming state, with attached depth gauge assembly 750 is advanced into medial collet 610 until the reamer head 706 contacts the patella. As the reamer is inserted, the position of depth gauge assembly 750 is adjusted. The depth gauge assembly is moved until the bottom surface 753 of the assembly 750 rests on the proximal end 602 of the medial collet 610. The depth gauge 752 is removed. The gap formed between the bottom 766 of the remaining depth stop 757 and the proximal end 602 is the proper reaming depth. The reamer 700 is powered to ream the patella medial facet through the medial collet 610 until the bottom 766 of the depth stop 757 contacts the proximal end 602 of the collet. The reamer 700 may be withdrawn from the medial collet 610. The depth gauge 752 is snapped back onto the depth gauge assembly 750, and the reaming procedure is repeated through the lateral collet 612, reaming the lateral facet of the patella 2. Referring to FIG. 22, the reaming of the medial and lateral facets of the patella 2 may create a prepared medial ridge 32 between medial and lateral reamed facet surfaces 36, 38. Differently sized reamer heads 706 may be used to produce differently sized medial and lateral reamed facet surfaces. The angle between the two reamed facet surfaces 36, 38, may match angle a of patellar implant 100 or 200 and matches angle c of reaming guide 600. If a flat reamer is used, the reamed facet surfaces 36, 38 are planar. If a convex reamer is used, the reamed facet surfaces 36, 38 include concavities. It is appreciated that both reamed facet surfaces 36, 38 can be reamed without requiring re-clamping of the patella, and that the surfaces can be reamed in either order. It is also appreciated that the depth stop assembly 750 can be independent of the clamping apparatus 510, and that the depth stop assembly 750 provides proper reaming depth determination across at least two divergent planes and along at least two divergent reaming trajectories.

The drill guide 850 may be inserted into the lateral collet 612 of the reaming guide 600 without re-clamping or adjusting the position of the patella. First and second 864, 866 rails are axially received in tracks 632, and third rail 868 is received in slot 630. The drill guide 850 may be slid into engagement within the collet 612 until alignment notch 875 rests on the prepared medial ridge 32 of the patella 2. Once the drill guide 850 touches the bone, it serves to indicate the location of the top of the patella, and thus controls the depth of the drill when it is inserted into the drill guide. Drill 700 is powered and advanced through each of the drill bores 880, 882, to drill holes for implant pegs or posts. The depth of each hole may be limited by contact of drill depth stop 808 with drill guide first end 852. The reaming guide 600 may be removed from the clamping apparatus 510 and a patellar implant fastened to the prepared patella, with implant pegs received in the holes. Cement may be used to attach the implant to the patella, and the cement may flow into recesses formed on the attachment surfaces of the implant, and/or into grooves on the implant recesses or pegs. In one example, if a flat reamer is used, the reamed facet surfaces 36, 38 may be planar and may complementarily match the attachment surfaces 132, 134 of implant 100. In another example, if a convex reamer is used, the reamed facet surfaces 36, 38 include concavities and may complementarily match the attachment surfaces 232, 234 of implant 200.

In FIGS. 13 through 20B, a resection assembly which may be used to create one or more resected surfaces on a patella posterior surface is shown. The resection may be preparation for implantation of an implant such as 100, 101, or 200, for example. Resection assembly 1000 includes a force-limiting clamp assembly 1050, an adjustable restraint arm assembly 1150, and a resection cutting guide 1200. Resection assembly 1000 may be used to securely clamp and/or restrain a patella while planar patellar resections are made along a medial resection trajectory 1002 and a lateral resection trajectory 1004. These trajectories maybe angled relative to one another by angle d, which may be the same as angle a and/or angle c as disclosed herein. Resection assembly 1000 may be referred to as a bi-planar, or a bi-planar/flat resection assembly.

Referring to FIGS. 5 and 13-16, clamp assembly 1050 may be removably mounted on clamping apparatus 510. Clamping assembly 1050 includes an attachment portion 1052 for connection to the clamping apparatus 510, a clamp body 1054 and a force-limiting mechanism 1056. Clamp body 1054 includes a clamping surface 1060 which may be a posterior clamping surface, which may have a notch 1062. One or more teeth 1064 may protrude from the clamping surface 1060. The clamping surface 1060 may be concavely curved as shown, or on other embodiments may be flat or convex. The force-limiting mechanism 1056 includes a first housing 1070 which may be a distal housing. The first housing 1070 includes a base portion 1072 through which a base passage 1074 extends, opening out on opposite sides of the base portion. A pin 1076 may be captured in the base passage 1074 and may travel the length of the base passage 1074. A boss portion 1078 protrudes proximally from the base portion 1072 and may be of a smaller diameter than the base portion. A spring 1082 encircles the boss portion and rests on a proximal end 1080 of the base portion 1072.

The force-limiting mechanism 1056 further includes a second housing 1086 which may be a proximal housing. Second housing 1086 may be generally cylindrical and tubular, with an interior bore 1088 defined by a housing wall 1090. A pair of transverse pin holes 1092 perforate the housing wall 1090 opposite one another, and are sized and shaped to receive pin 1076. The interior bore 1088 includes a proximal bore section 1094 and a distal bore section 1096; the diameter of the proximal bore section 1094 is sized to receive the boss portion 1078, and is less than the inner diameter of the spring 1082. The diameter of the distal bore section 1096 is sized to receive the base portion 1072 when the force-limiting mechanism 1056 is operatively assembled. When assembled as in FIG. 15, spring 1082 is captured in distal bore section 1096, between proximal end 1080 of the base portion 1072 and a shoulder 1098 of the proximal bore section 1094 of the second housing 1086. On the exterior of the second housing 1086 may be indicia. For example, indicia may include cross hairs 1100, including a medial ridge line 1102 and an inferior/superior center line 1104. On the clamp body 1054, a continuation of the medial ridge line 1102a and of the inferior/superior center line 1104a may be found. The cross hairs 1100 and continuation lines 1102a, 1104a may be used by a practitioner to properly position a patella in the resection assembly in order to control the final location of the peak of the spherical dome on the posterior articulation surface of the implant, for example 116 or 216.

Figure 17:
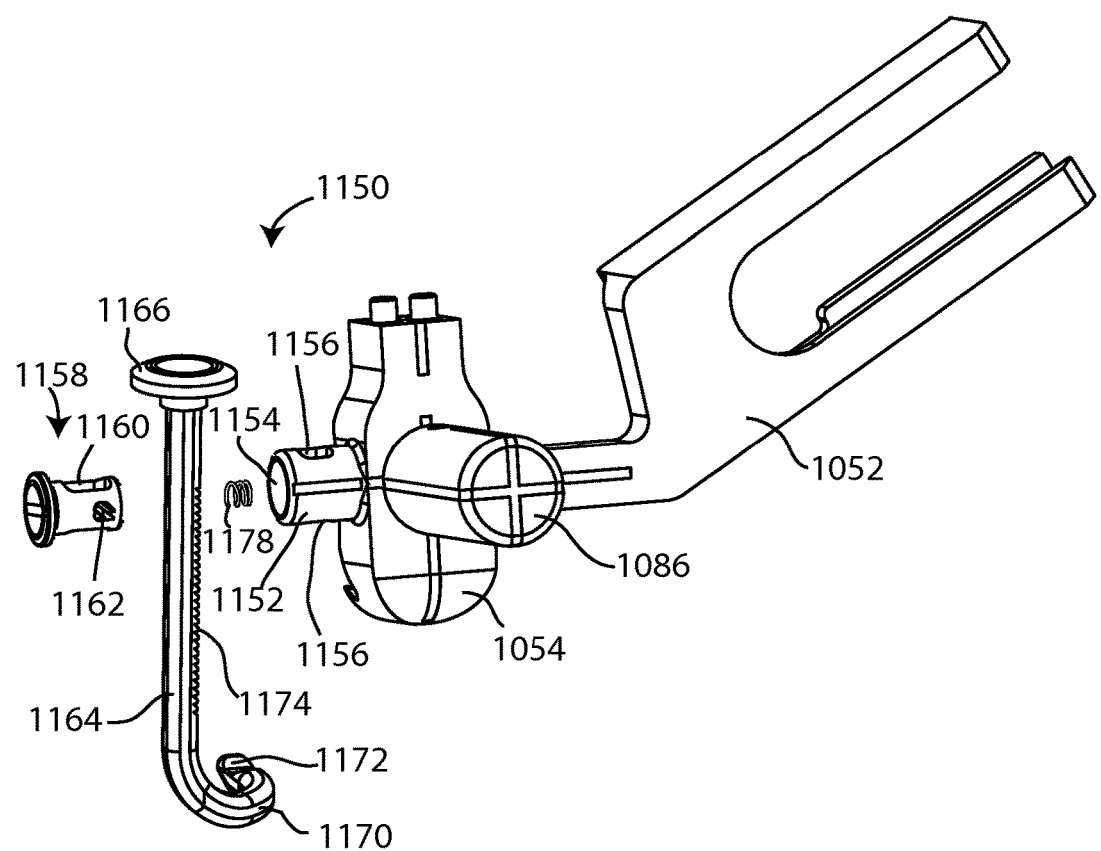
FIG. 17 is a partially exploded view of the force-limiting clamp assembly and adjustable restraint arm assembly of FIG. 13.
Figure 18:
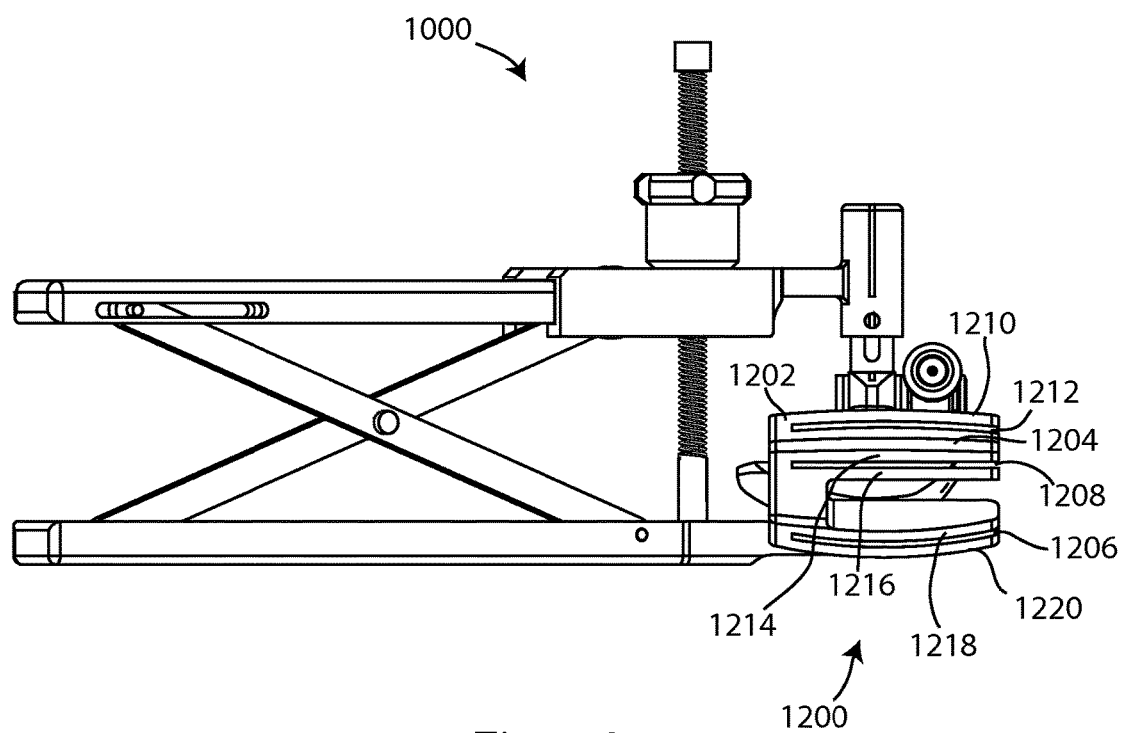
FIG. 18 is a medial side view of the resection assembly of FIG. 13.

Referring to FIG. 17, an exploded view shows detail of restraint arm assembly 1150. Clamp body 1054 includes a dock 1152 which may project laterally from the clamp body and carries a restraint arm. A plug bore 1154 extends through at least a portion of dock 1152. Traverse to plug bore 1154, an arm opening 1156 extends through opposite sides of the dock. A plug 1158 is sized to be received in the plug bore 1154. Plug 1158 includes an arm slot 1160 extending through the plug. In communication with the arm slot 1160 and formed into the plug 1158 is at least one flange 1162 which protrudes into the arm slot 1160. A restraint arm 1164 includes a proximal arm end cap 1166, an arm shaft 1168, and a distal restraint end 1170. The restraint end 1170 curves generally perpendicularly away from the shaft 1168 and may include a divot 1172 or other feature for receiving a patella. A plurality of ratchet teeth 1174 can be incised along a portion of the restraint arm 1164.

When restraint arm assembly 1150 is operatively assembled, a plug spring 1178 is received in plug bore 1154. Plug 1158 is received in plug bore 1154, capturing the spring 1178 in the plug bore 1154. Restraint arm 1164 is extended through arm openings 1156 and arm slot 1160; cap 1166 may be removable for assembly purposes. Ratchet teeth 1174 mesh with flanges 1162 and the spring bias of spring 1178 holds and locks the arm 1164 at a selected position relative to dock 1152. The position of arm 1164 can be adjusted by pressing plug 1158 toward dock 1152 to overcome the spring bias and unlock or release teeth 1174 from flanges 1162. The arm may be translated through arm openings 1156 and arm slot 1160 to another position, and plug 1158 released to lock the arm in the newly selected position.

In other embodiments, the restraint arm 1164 may also be rotatable, in addition to translatable, relative to the clamp body 1054. For one example, the dock 1152 carrying the arm 1164 may be selectively rotatable relative to the claim body. In another example, the restraint arm 1164 may be selectively rotatable relative to the dock.

Referring to FIGS. 13, 15A, 15B, and 18, the resection cutting guide 1200 includes cutting guide body 1202 which may be formed integrally with clamping body 1054 or may be selectively detachable. The cutting guide 1200 includes at least one resection guide feature, which may be a slot for guiding a blade or saw 1250 in resecting a patellar surface. As seen in FIG. 15, one example of a cutting guide body 1202 includes a lateral facet resection slot 1204, a medial facet resection slot 1206, and a flat resection slot 1208 which may be intermediate the lateral and medial facet resection slots. Each resection slot may be defined by an upper and lower plate on either side of the slot, the plates providing planar surfaces parallel to the slot to rigidly guide a blade such as saw 1250. Lateral facet resection slot 1204 is defined by upper lateral slot plate 1210 and lower lateral slot plate 1212. Flat resection slot 1208 is defined by upper flat slot plate 1214 and lower flat slot plate 1216. Medial facet resection slot 1206 is defined by upper medial slot plate 1218 and lower medial slot plate 1220. The plates may be joined together at the cutting guide body 1202. The heights and widths of the slots may vary to accept differently sized blades.

Figure 19:
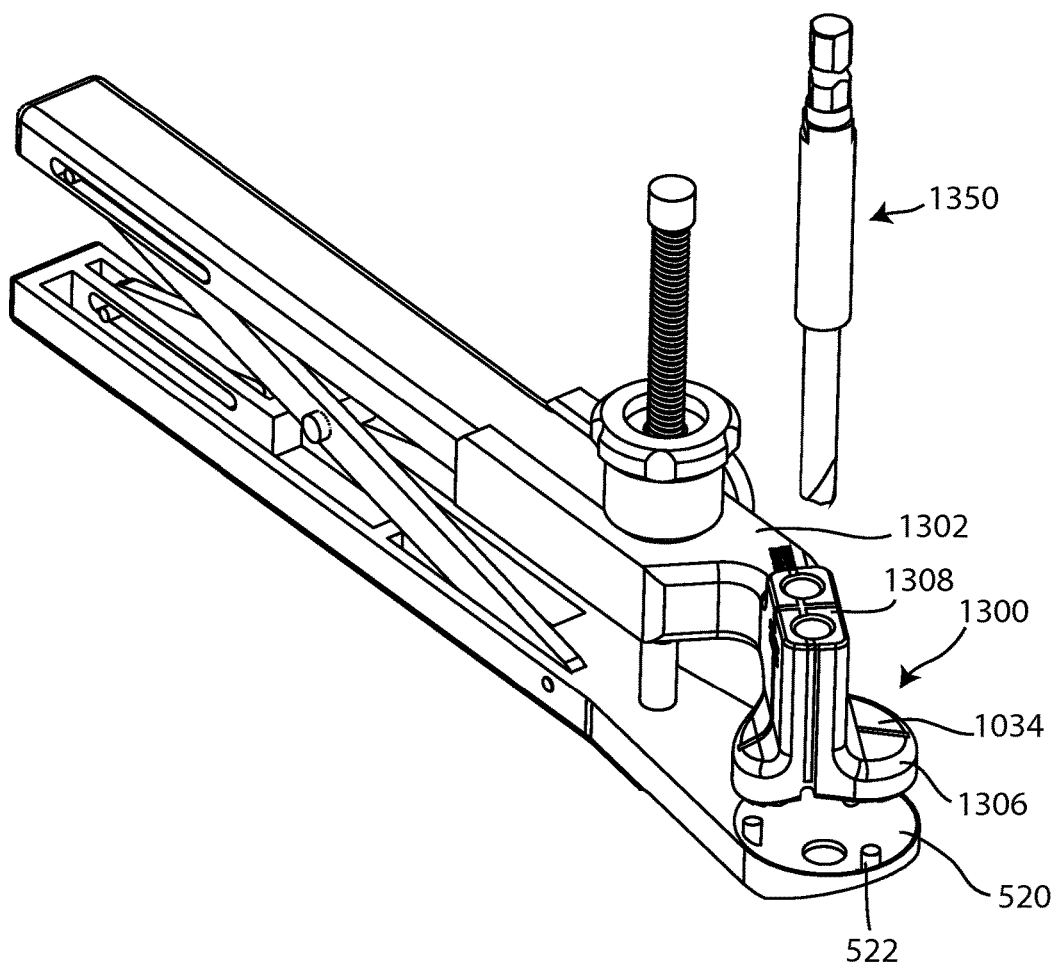
FIG. 19 is a partially exploded perspective view of the clamping apparatus of FIG. 13 with a another drill guide mounted on the apparatus, and a another drill.
Figure 20A:
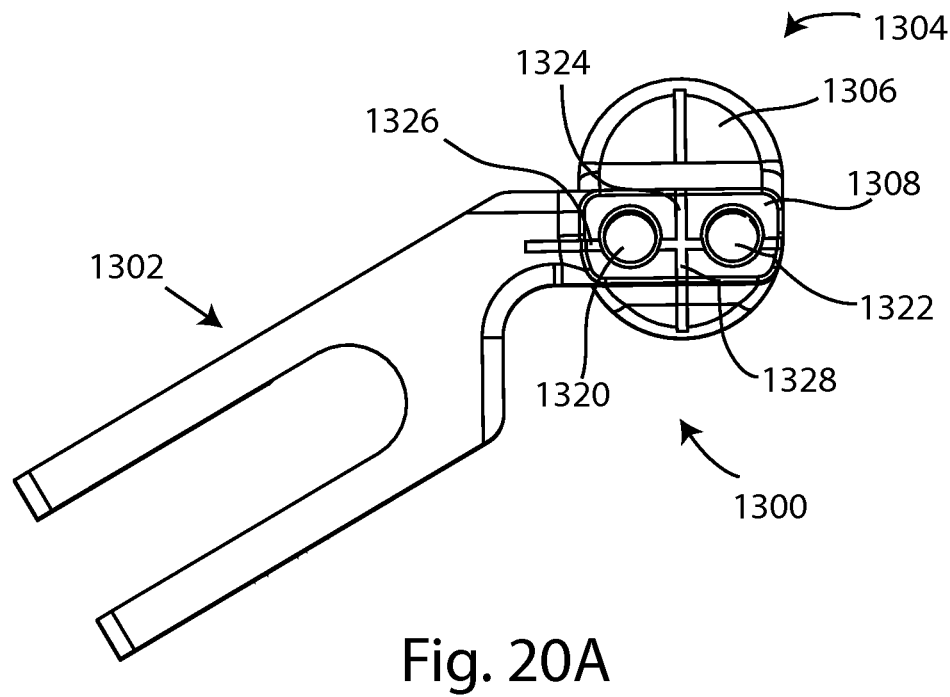
FIG. 20A is a top view of the drill guide of FIG. 19.
Figure 20B:
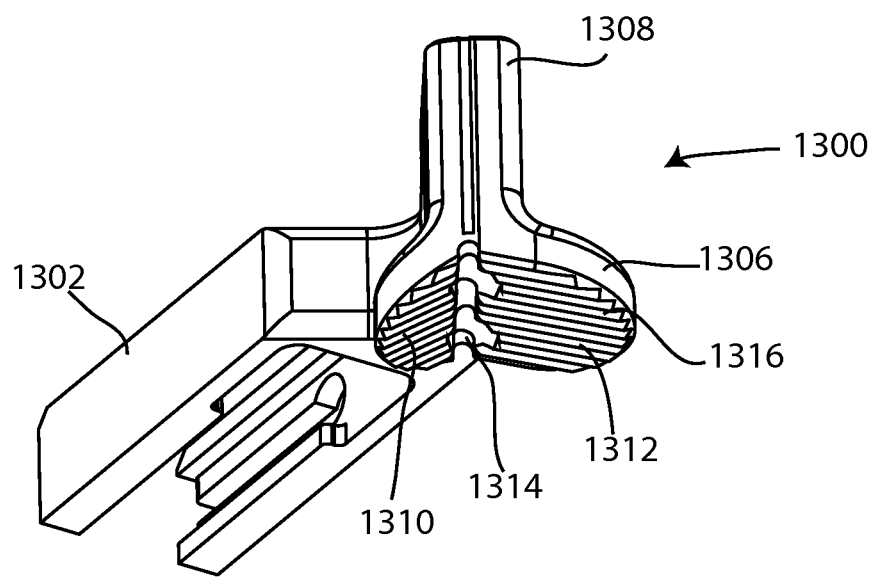
FIG. 20B is a bottom perspective view of the drill guide of FIG. 19.

Referring to FIGS. 19, 20A and 20B, a drill guide and drill for guiding drilling of implant peg or post holes is shown. Drill guide 1300 includes an attachment portion 1302 and a drill guide body 1304. Drill guide body 1304 includes a foot portion 1306 and a drill guide portion 1308. Foot portion 1306 includes a medial foot 1310 and a lateral foot 1312, and a groove 1314 intermediate and separating the medial and lateral feet 1310, 1312. The medial 1310 and lateral 1312 feet provide a bi-planar clamping surface which can self-align with resected bi-planar surfaces on a prepared patella. A plurality of gripping features such as teeth or ridges 1316 may be formed on the feet 1310, 1312. First and second drill bores 1320, 1322 extend through the drill guide portion 1308 and open out at the foot portion 1306. The first and second drill bores 1320, 1322 may be laterally offset relative to the groove 1314. A set of crosshairs 1324 including a medial ridge line 1326, an inferior/superior center line 1328, and respective continuation lines like those set forth above with regard to the clamp body 1054, may be present on the drill guide. Drill 1350 includes an attachment section 1352 for attachment to a powered drive, a drill shaft 1354, and a bit 1356. A drill depth stop 1358, which may be shaped as a collar, is formed on a portion of the drill.

Figure 13:
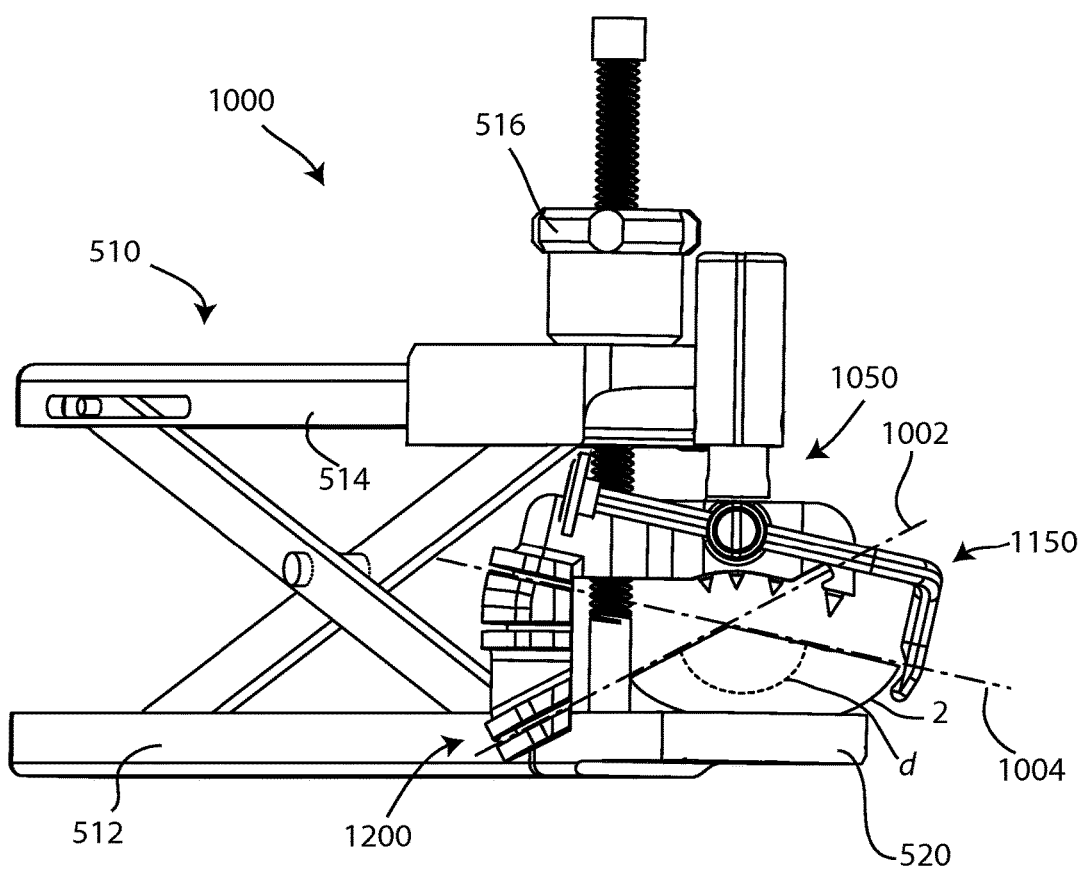
FIG. 13 is a perspective view of a resection assembly including a modular clamping apparatus, a force-limiting clamp assembly, an adjustable restraint arm assembly, and a resection cutting guide, a resected patella on an anterior clamp of the resection assembly.
Figure 14:
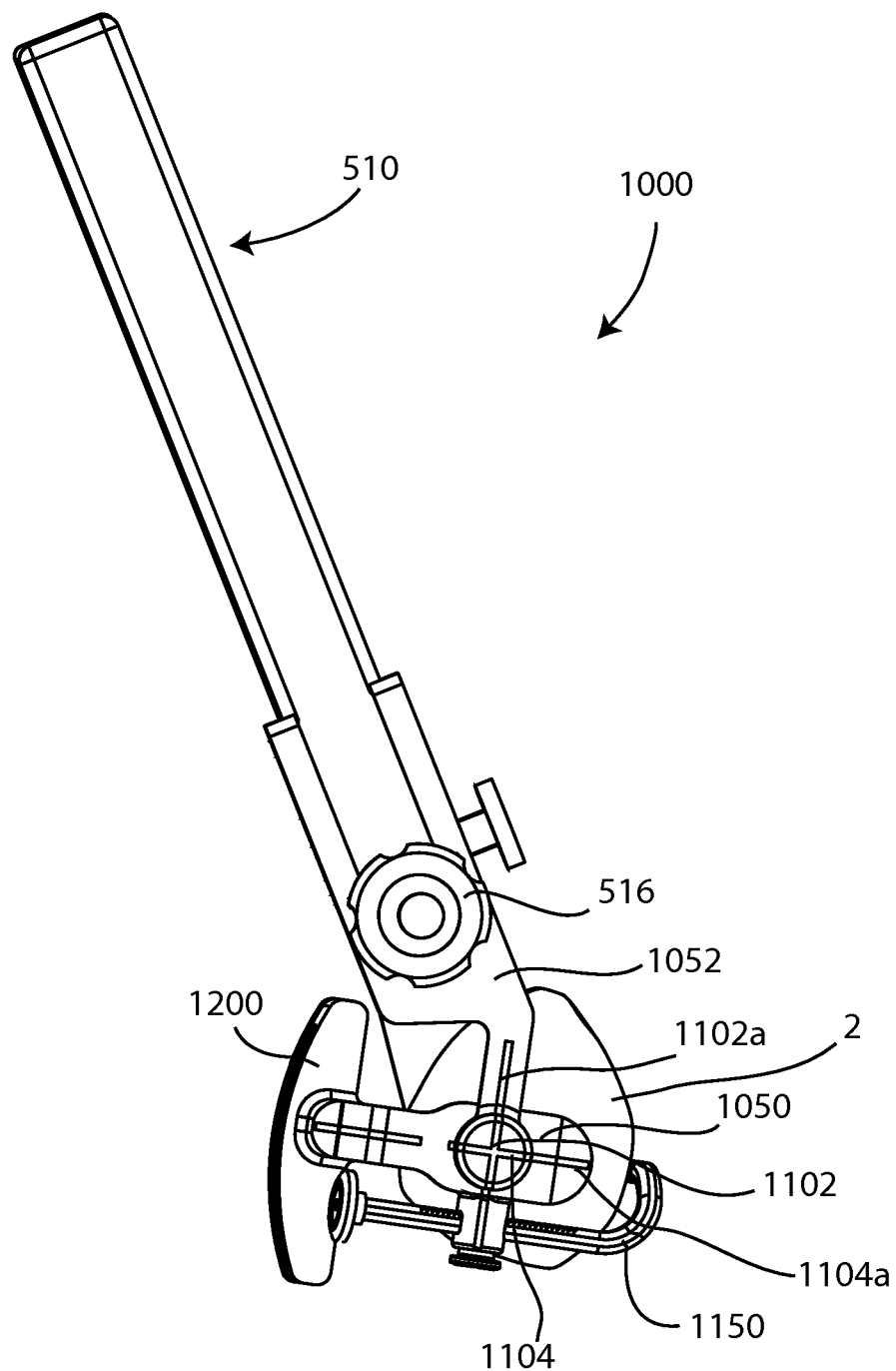
FIG. 14 is a top view of the resection assembly of FIG. 13, showing cross hairs and lines for orienting a patella in the clamping apparatus.

With reference to FIGS. 13 through 20B, one method of preparing a patella is described, using resection assembly 1000. Patella 2 may be positioned on anterior clamp 520 and positionally adjusted for proper anatomic alignment. The practitioner views the assembly and patella from a top down perspective, as seen in FIG. 14. The cross hairs 1100, lines 1102, 1104 and continuation lines 1102a, 1104a are viewed in relation to the patella, and the patella 2 may be positioned so the natural patellar medial ridge is lined up with the medial ridge lines 1102, 1102a. Alternatively, the patella may be positioned so that a desired location for a prepared medial ridge is lined up with the medial ridge lines 1102, 1102a. Selection of a desired location may be based on the relative health of the available bone material.

When the patella is selectively positioned on the anterior clamp 520, clamp assembly 1050 is lowered toward the exposed posterior surface of the patella to clamp the patella between the anterior clamp 520 and the posterior clamping surface 1060. Teeth 1064 may assist in gripping the patella. As clamping occurs, compressive force is applied to the clamp assembly 1050 and the patella, but the force applied to the patella is limited by the spring 1082 of the force-limiting mechanism 1056. As force is applied to the modular clamping apparatus, the spring 1082 begins to deflect and compressive force is applied to the patella. As a result, the amount of compressive force applied to the patella is directly related to the amount of spring deflection and not the amount of load applied to the modular clamping apparatus. This may reduce the occurrence of over clamping the patella which can lead to saw binding during the resection procedure.

Figure 15A:
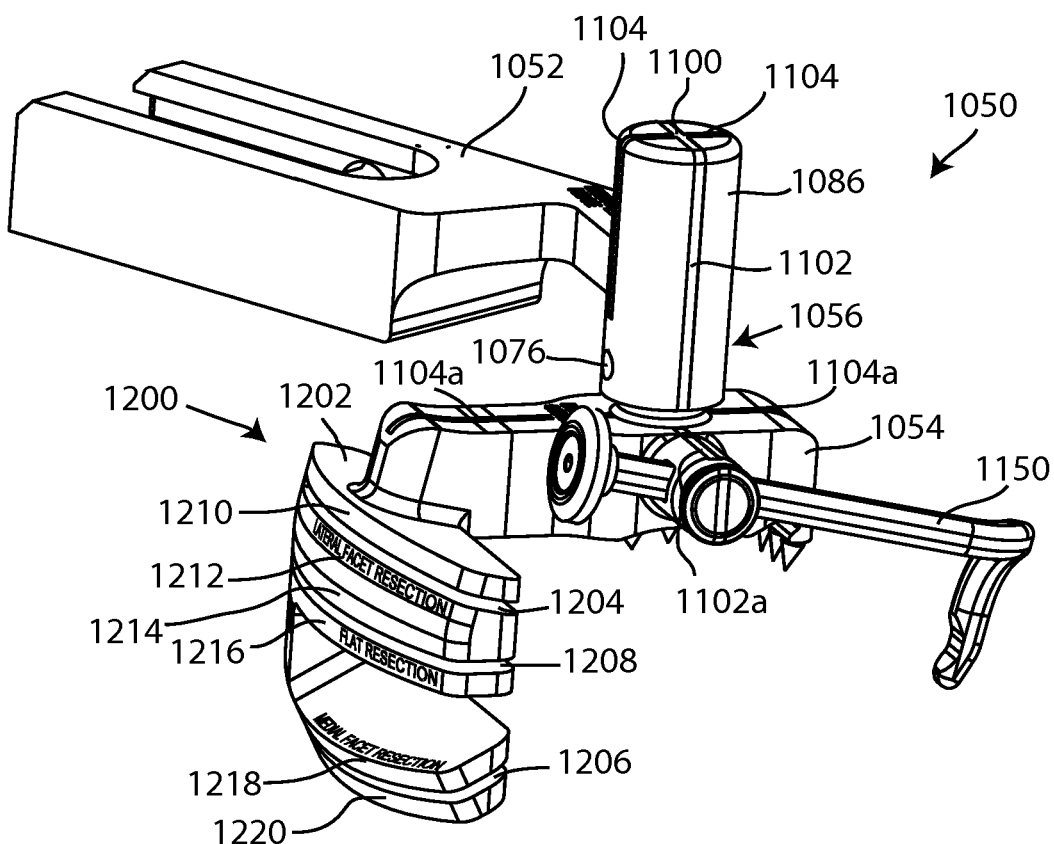
FIG. 15A is a perspective view of the force-limiting clamp assembly, adjustable restraint arm assembly, and resection cutting guide of FIG. 13.
Figure 15B:
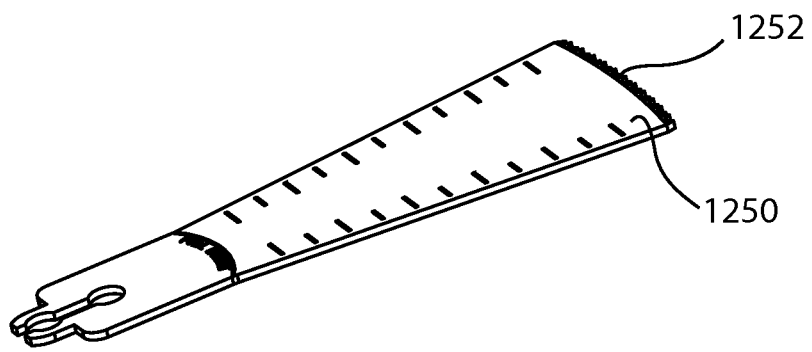
FIG. 15B is a sawblade suitable for use with the resection cutting guide.

The restraint arm assembly 1150 may be actuated to provide lateral restraint to the clamped patella. The restraint arm 1164 may be ratcheted as set forth previously to translate the arm 1164 until distal restraint end 1170 is brought into contact with the patella, which may be at the lateral edge of the patella. The restraint arm may provide a rigid supporting arm that creates the reaction forces necessary to provide a stable clamping mechanism. With the clamps 520, 1060 and restraint arm 1164 in place, the patella is firmly clamped anteriorly, posteriorly, and laterally. A sawblade 1250 as seen in FIG. 15B, or other cutting edge is inserted through medial facet resection slot 1206 and actuated to resect the patella along the medial resection trajectory 1002. An end 1252 of the sawblade or cutting edge may be captured in notch 1062. The sawblade is inserted through lateral facet resection slot 1204 and the patella is resected along the medial resection trajectory 1004. The resections may be performed in either order. Following resection, clamp assembly 1050 along with restraint arm assembly 1150 and resection cutting guide 1200 may be detached from clamping apparatus 510. The resected patella may remain on the anterior clamp 520.

Peg or post holes suitable for receiving, for example, pegs 138 or 238 may be drilled into the resected patella using drill guide 1300. Drill guide 1300 may be attached to clamping apparatus 510, and adjusted until foot portion 1306 is in contact with the resected patella, with medial foot 1310 contacting prepared medial facet 28 and lateral foot 1312 contacting prepared lateral facet 30. The prepared medial ridge 32 is aligned with and partially received in groove 1314. Crosshairs 1324 and lines 1326, 1328 may be viewed to assist in properly aligning the foot portion 1306 with the patella. The patella 2 is clamped between anterior clamp 520 and foot portion 1306, which functions as a posterior clamp. Drill 1350 is guided through drill bores 1320, 1322 to drill one or more holes in the patella.

Figure 21:
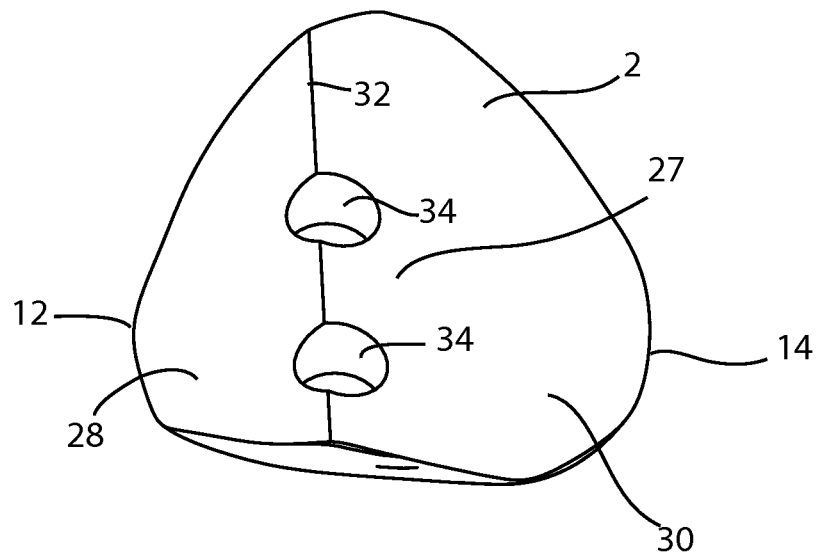
FIG. 21 is a posterior perspective view of a patella resected and drilled according to methods disclosed herein using instrumentation shown in FIGS. 13-20B.

FIG. 21 shows a resected patella 2 which may be produced by the methods set forth with reference to FIGS. 13-20B. The posterior surface has been prepared to form a prepared patellar surface 27 which includes the prepared medial facet 28, the prepared lateral facet 30, divided by the prepared medial ridge 32. Two peg holes 34 are recessed into the prepared surface 27, and are slightly offset toward the prepared lateral facet 30, relative to the medial ridge 32. The resections extend to the outer borders of the patella. A patellar implant such as implant 100 described above, or an onlay implant may be attached to the prepared patella as described previously.

FIG. 22 shows a reamed patella 2 which may be prepared by the methods set forth with reference to FIGS. 5-12. The posterior surface has been prepared to form a prepared patellar surface 35 which includes a reamed medial facet 36 and a reamed lateral facet 38, divided by the prepared medial ridge 32. The reamed areas are inset or recessed into the posterior side 6. Two peg holes 34 are recessed into the prepared surface 35, and are slightly offset toward the reamed lateral facet 38, relative to the medial ridge 32. The reamed areas may extend to the outer borders of the patella, or may be spaced apart from the medial and/or lateral borders. A patellar implant such as implant 200 described above, or an inlay implant may be attached to the prepared patella as described previously.

Prior to implantation or attachment of a patellar implant, a patellar trial may be positioned on the patella. The height, or thickness of the prepared patella and trial may be measured and compared with a desired height. If the measured height is substantially equal to the desired height, the implant may be attached with cement or other materials. In one embodiment, the measured height is considered substantially equal to the desired height if the two measurements are within 1+/−1 millimeter, or 2 millimeters or less.

As described previously, cement may be used to attach the implant to the patella, and the cement may flow into recesses formed on the attachment surfaces of the implant, and/or into grooves on the implant recesses or pegs. The cement may form a mantle between the prepared patellar surface and the anterior attachment surface of the implant.

Figure 23:
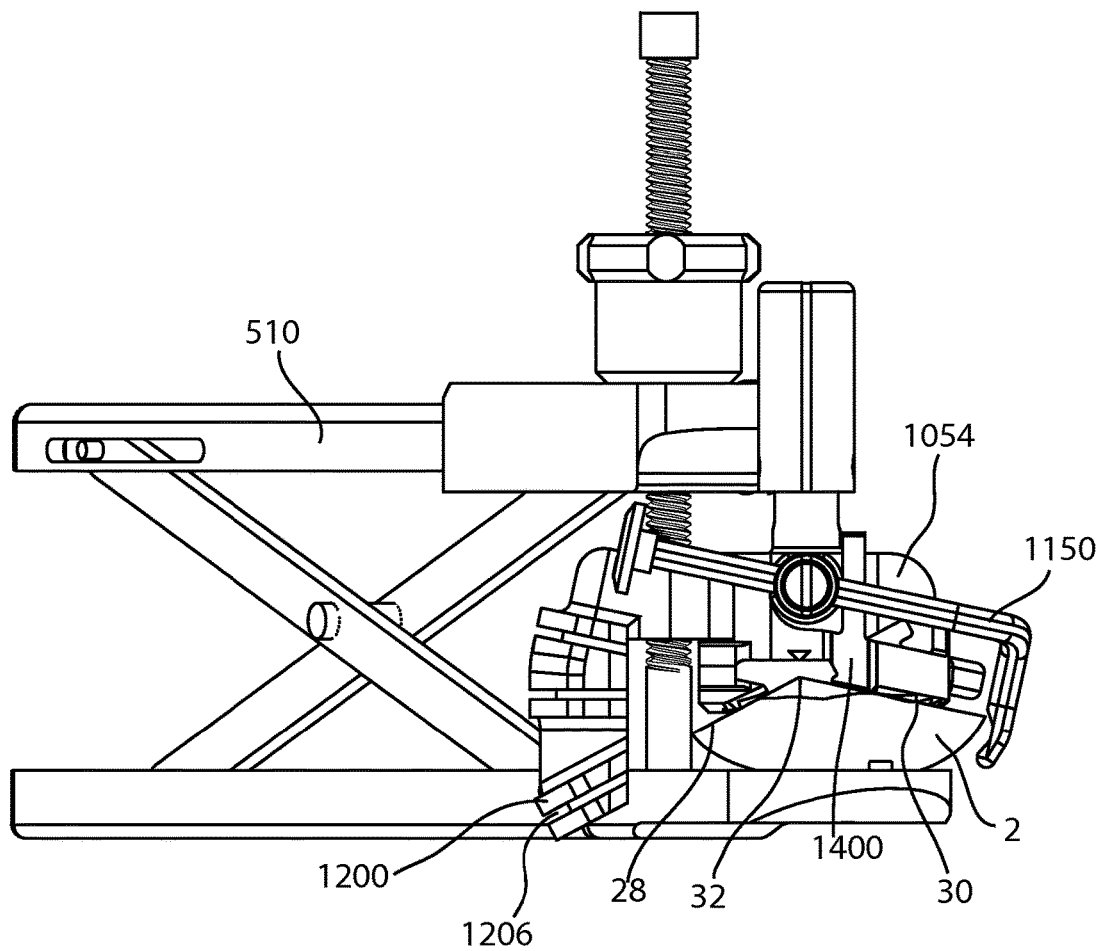
FIG. 23 is a perspective view of the resection assembly of FIG. 13 with a recut spacing guide and a resected patella.
Figure 24A:
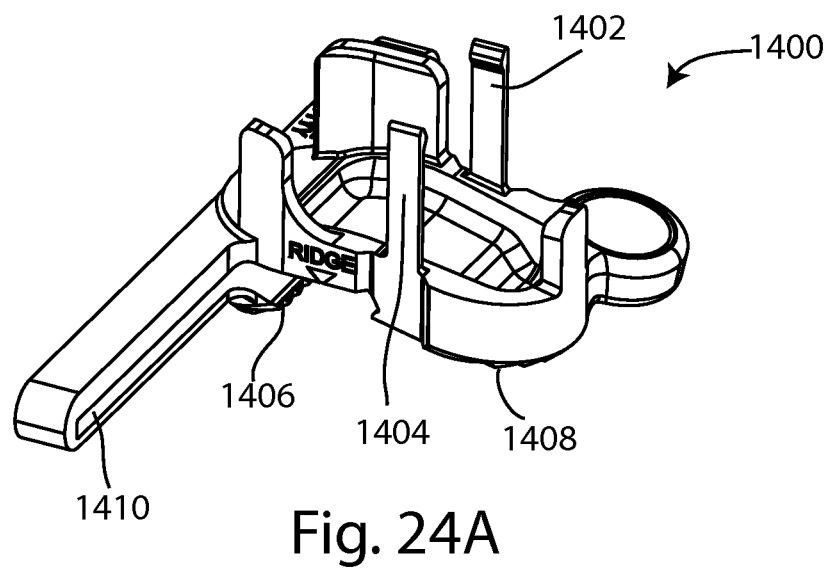
FIG. 24A is a perspective view of the recut spacing guide of FIG. 23.
Figure 24B:
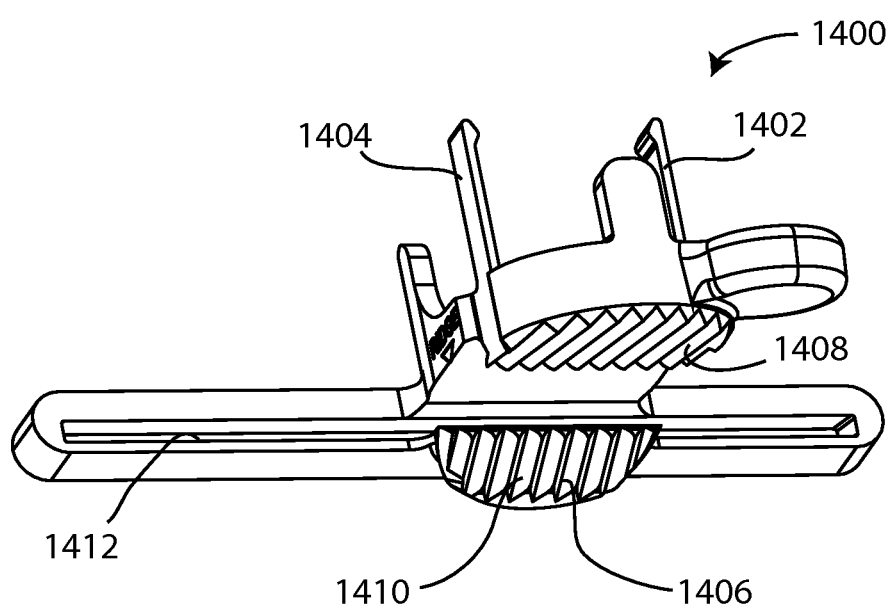
FIG. 24B is a bottom perspective view of the recut spacing guide of FIG. 23.

FIGS. 23-24B show a recut spacing guide that may be used with resection assembly 1000 if measurement of a resected patella shows that the resected patella is taller than desired. Recut spacing guide 1400 may be snapped via tabs 1402, 1404 or otherwise coupled onto clamp body 1054. The spacing guide 1400 includes a medial foot 1406 and a lateral foot 1408. The feet 1406, 1408 may include ridges 1410, teeth or other engagement features to ensure a secure contact with the resected patella. Space is provided between the medial and lateral feet to allow for the medial ridge of the patella. The trajectory of a cutting slot 1412 is parallel with the lateral foot 1408. The recut spacing guide may be sized to provide additional resection cuts of, for example, 1 mm, 2 mm, or any other desired height.

In a method of use, the recut spacing guide is snapped on to clamp body 1054 and lowered via clamping apparatus 510 until the medial and lateral feet 1406, 1408 rest on the resected medial and lateral facets 28, 30, respectively. The resected facets 28, 30 are further resected by inserting sawblade 1250 or other cutting edge through the medial facet resection slot 1206 and resecting the medial facet 28, and by inserting the cutting edge through the lateral facet resection slot 1204 and the cutting slot 1412 and resecting the lateral facet 30. The additional resections can be made in either order. Following resection, the patella can again be measured. If the desired height has been attained, a patellar implant may be attached. If additional resection is needed, the steps above may be repeated until the desired height is attained.

Patellar implants and instrumentation for preparation of the patella and implantation of patellar implants, including those described herein, may be customized to match a patient's natural anatomy. In an embodiment, a method for creating and implanting a patient specific implant may include one or more of the following steps: (1) pre-operative imaging studies of a patient's native patella including, but not limited to, digital CT Scans, digital MRI Scans, X-ray digital data, ultrasound, digital tomo-synthesis, optical coherence tomography, and/or any other technologies derived for converting patient anatomy to digital data; (2) a detailed review of the imaging studies to determine measurements and parameters for patient specific implant and/or instrumentation; (3) manufacturing a patellar implant that is optimized for the patient, based on the pre-operative measurements of the patient's native patella; (4) manufacturing and/or assembling instruments optimized for the patient including the anterior (or dorsal) geometry of the patella anatomy to achieve pre-operatively planned alignment, the posterior profiles of the inferior and superior soft tissues of the patella, and the bony perimeter of the patella in the anterior-posterior projection; (5) providing surgeon guidance on correct reaming collet size, reamer size, and/or optimal reaming depth; (6) preparation of the native patella using one or more of the patient specific instruments described herein, and/or another instrument option; and (7) implanting a patient specific patellar implant into the prepared native patella.

Patient specific patellar implant and instrumentation for patellar preparation may be manufactured using measurements of the patient's natural patella and surrounding tissues. With reference to FIGS. 1A-1C, specific measurements of the patient's patella may include, but are not limited to: a) width (medial/lateral); b) length (superior/inferior); c) thickness or height (anterior/posterior); d) location of the vertical ridge 16; e) the angles of the medial and lateral facets; f) the outer shape, or footprint of the patella when viewed from an anterior or posterior perspective; g) the topography of the anterior side 4; and h) the topography of the posterior, or articular side 6.

The posterior, or articular surface of a patient specific patellar implant can be customized to match the articular surface 6 of the patient's natural patella. The natural patella is measured using any of the imaging methods set forth above, and/or by direct visualization and direct measurement. The measurements of the natural patella are used to determine at least one of the following parameters of the patellar implant: a) implant width, b) implant length, c) implant thickness; d) spherical dome radius; e) location of the dome (both medial/laterally and inferior/superiorly); f) facet angle; g) location of a medial ridge; and h) length of the medial ridge.

Figures 25A, 25B:
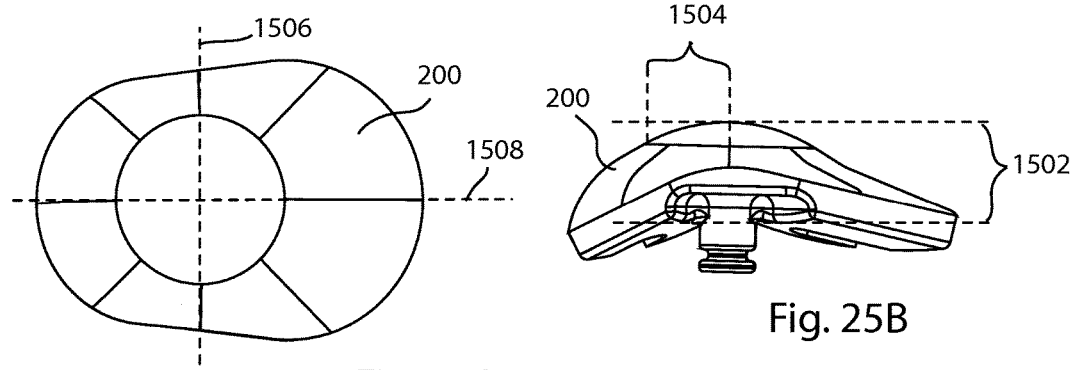
FIG. 25A is a posterior view of the patellar implant of FIG. 4A, showing alignment of a dome of the implant.
FIG. 25B is a superior view of the patellar implant of FIG. 4A, showing dome radius and implant height measurements.
Figures 26A, 26B:
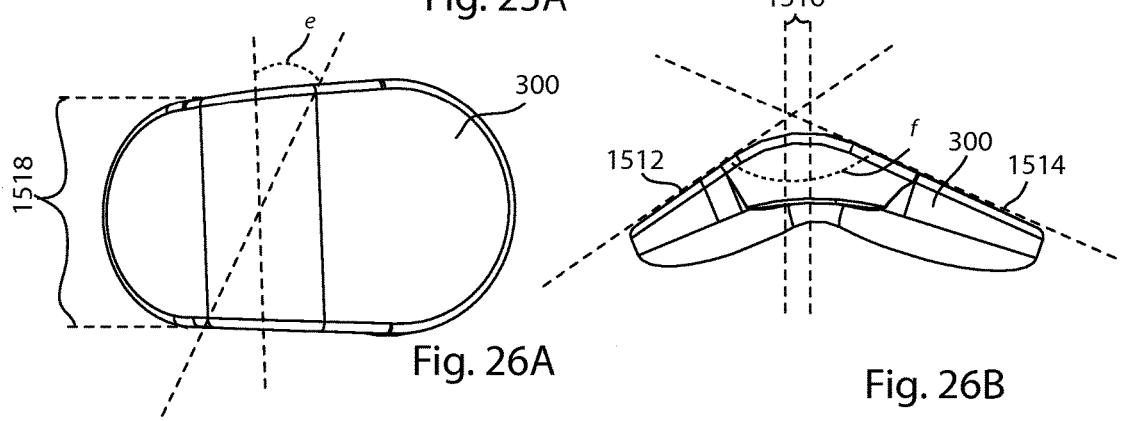
FIG. 26A is a posterior view of a patellar implant having a medialized ridge, showing an orientation angle of the ridge.
FIG. 26B is a superior view of the patellar implant of FIG. 26A, showing the ridge location and facet angle.
Figures 27A, 27B:
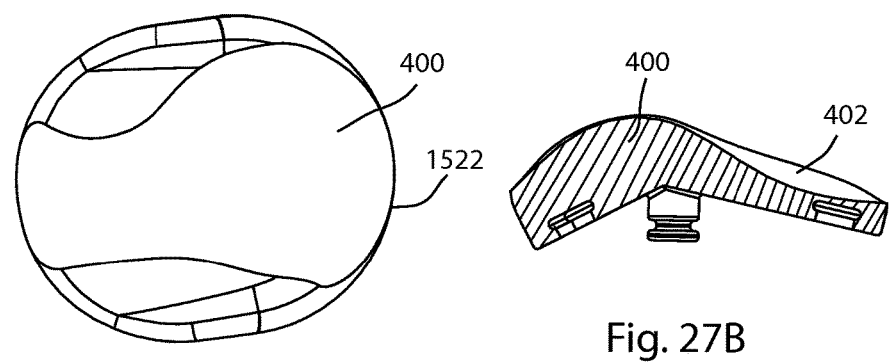
FIG. 27A is a posterior view of a patient specific patellar implant having an irregular articular surface.
FIG. 27B is a superior view of the patellar implant of FIG. 27A.

Referring to FIGS. 25A and 25B, a patellar implant having a domed articular surface, such as implants 100, 101, or 200, may include one or more of the following customized parameters: implant length, implant width, implant thickness 1502, dome radius 1504, dome location to include medial/lateral position 1506 and inferior/superior position 1508, and medial 1512 and lateral 1514 facet angle e. A patellar implant having a ridged articular surface, such as implant 300 in FIGS. 26A and 26B, may include one or more of the following customized parameters: implant length, implant width, implant thickness 1502, location of the medial ridge (medial/lateral position) 1516, length of the medial ridge 1518, ridge orientation angle f facet angle e. Referring to FIGS. 27A and 27B, a highly customized patellar implant such as 400 having a non-symmetrical, irregular articular surface 402 may include one or more of the following customized parameters: implant length, implant width, implant thickness 1502, articular surface topography, and outer shape or footprint 1522. Any of the patellar implants disclosed herein, for example implant 100, may have a customized anterior attachment surface in which the angle a between the medial and lateral attachment surfaces is manufactured to match the facet angle of the native patella. A patellar implant that is based on patient specific natural anatomy, as disclosed herein, may achieve an articular surface that is highly conforming to the mating surface on the femoral component of a knee prosthesis, or to the natural femoral articular surface.

The instrumentation used to prepare the patella for the implantation of a patellar implant may also be customized using patient specific data. Specific measurements which may be taken using the imaging methods disclosed herein, in addition to those disclosed above may include, among others: a) the outer profile of the patella bony mass; b) the posterior profile of the soft tissue inferior to the patella; c) the posterior profile of the soft tissue superior to the patella; d) the topology of the anterior, or dorsal surface of the patella. These measurements may be used to manufacture patient specific instruments as set forth below.

Figure 28:
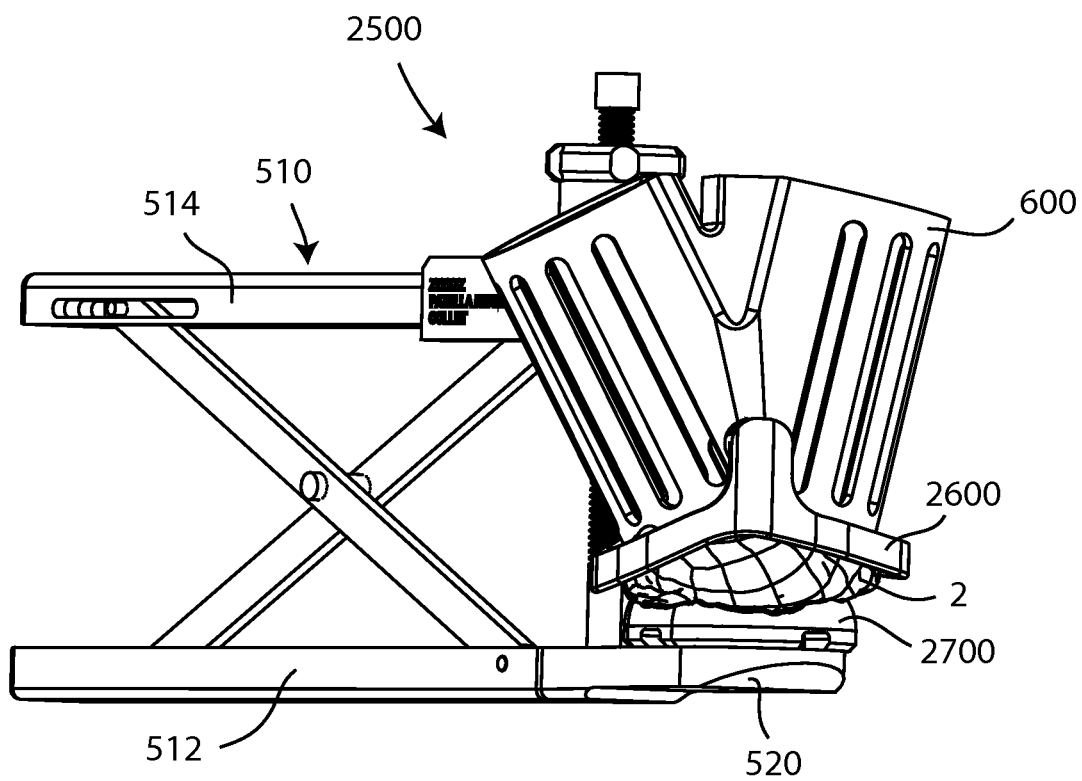
FIG. 28 is a perspective view of the modular clamping apparatus and dual axis reaming guide of FIG. 5 with a patient specific clamping ring and a patient specific anterior camp insert, with a patella clamped within the clamping ring, and between the dual axis reaming guide and the anterior clamp insert.

In one embodiment, a patella preparation instrument assembly includes instruments which are custom sized and/or shaped based on measurements from a patient's native patella and surrounding tissues. Referring to FIG. 28, instrument assembly 2500 includes previously described modular clamping apparatus 510, on which the dual axis reaming guide 600 is mounted. A patella 2 is clamped in the clamping apparatus. A retaining member which may be characterized as a clamp ring 2600 encircles the periphery 15 of the patella, and the anterior side of the patella abuts a dorsal clamp insert 2700 mounted on the anterior clamp 520 of the clamping apparatus 510. The clamp ring 2600 is removably mounted to the dual axis reaming guide 600. Both the clamp ring 2600 and the dorsal clamp insert 2700 are dimensioned according to measurements specific to the patient's patella.

Figure 29A:
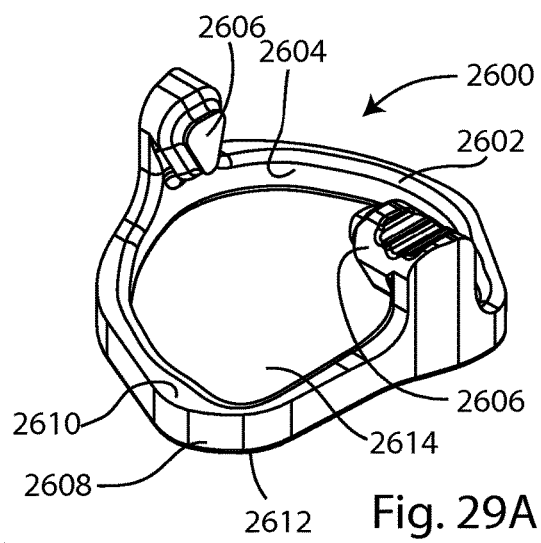
FIG. 29A is a perspective view of the patient specific clamping ring of FIG. 28.
Figure 29B:
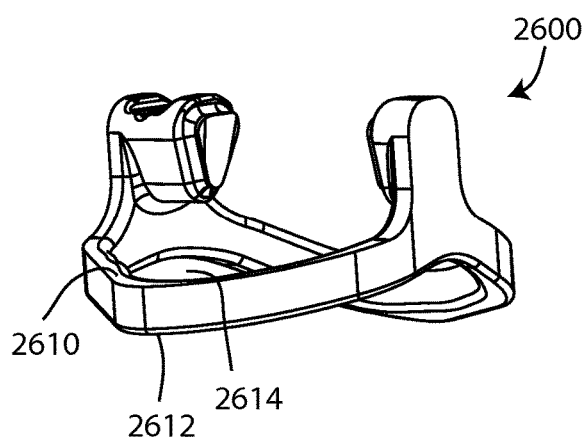
FIG. 29B is another perspective view of the clamping ring of FIG. 28.
Figure 29C:
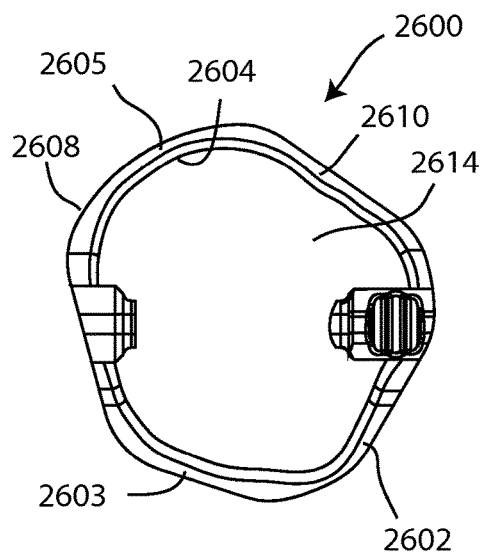
FIG. 29C is a top view of the clamping ring of FIG. 28.
Figure 32A:
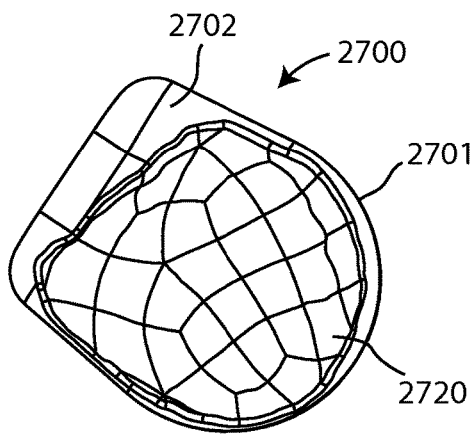
FIG. 32A is a top view of the patient specific anterior clamp insert of FIG. 28.
Figure 32B:
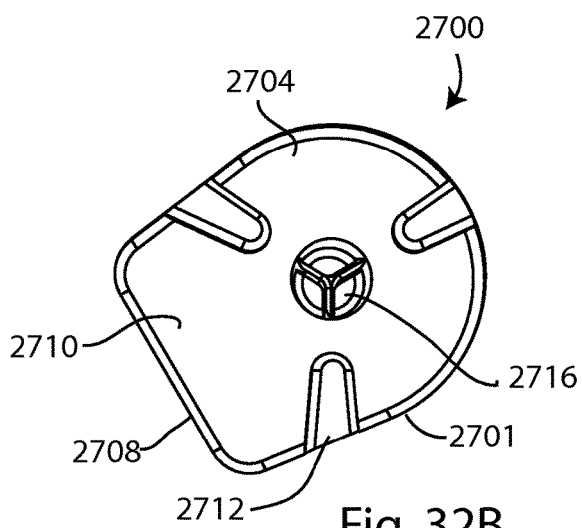
FIG. 32B is a bottom view of the anterior clamp insert of FIG. 28.
Figure 32C:
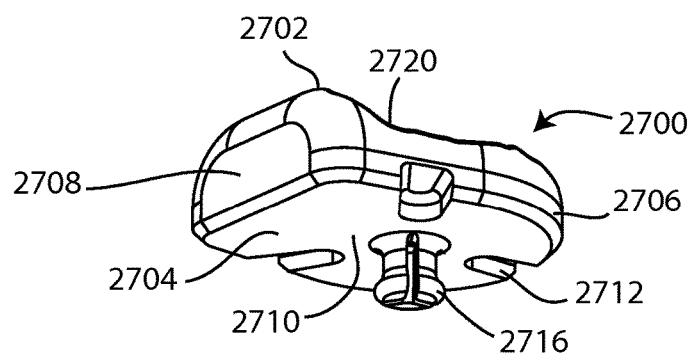
FIG. 32C is a bottom perspective view of the anterior clamp insert of FIG. 28.
Figure 32D:
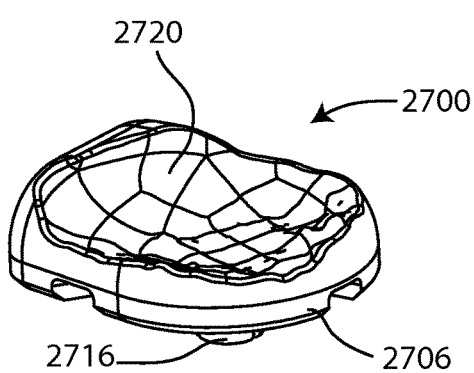
FIG. 32D is a top perspective view of the anterior clamp insert of FIG. 28.
Figure 32E:
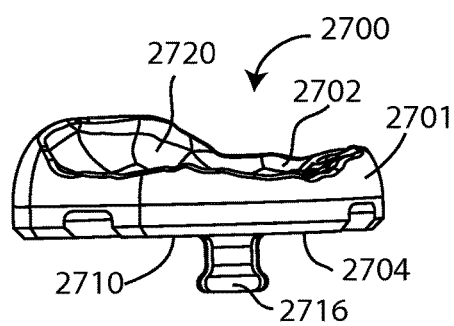
FIG. 32E is a side view of the anterior clamp insert of FIG. 28.

The clamp ring 2600 is shown in further detail in FIGS. 29A-29C. In an embodiment, the clamp ring functions as a constraint structure for the patella, firmly holding the patella and associated soft tissues in a fixed position in order to allow precise alignment of the clamping apparatus, and associated reaming guide and/or resection guide relative to the patella and soft tissue associated with the patella. The patient-specific clamp ring 2600 comprises a continuous strip forming a closed loop. The clamp ring 2600 includes an annular ring portion or ring body 2602, the shape of which can be customized based on patient-specific data. The inner surface of the ring portion is an inner clamping surface 2604 for facing and gripping the patella; the inner clamping surface 2604 which may also be customized based on patient-specific data. An outer surface 2608 bounds the outer periphery of the ring portion 2602. Both the inner and outer surfaces 2604, 2608 may be irregularly shaped, reflecting the irregular periphery 15 of the native patella. In an embodiment, the outer surface 2608 may be regular, for example circular or rectangular, while the inner clamping surface 2604 is irregular to complement the periphery of the patella and to grip the patella. The inner surface 2604 may include ridges, grooves or other surface treatments or roughening to increase clamping contact with the patella. In an embodiment, the ring portion and/or either of both of the inner and outer surfaces 2604, 2608 may be circular. In an embodiment, the ring body and/or either or both of the inner and outer surfaces 2604, 2608 may be non-circular or irregular. In the context of this application, an annulus or annular shape is ring-shaped, but not necessarily circular, an annulus may be irregularly shaped. The ring body 2602 includes a medial ring portion 2603 and a lateral ring portion

2605. The medial and lateral portions may be differently shaped from one another, and may meet at the locations of attachment features 2606. Each medial and lateral portion may be roughly formed as a half circle, but have an irregular shape as seen in FIG. 29C.

The ring portion 2602 further includes a first edge 2610 which in the context of FIG. 29A appears as an upper edge, and a second edge 2612 which appears as a lower edge. The first and second edges 2610, 2612 may undulate, as best seen in FIG. 29B, to match the periphery of the patella and/or the patellar facets. The undulation of the first and second edges may be matched as in FIG. 29B or in other embodiments may be disparate relative to one another. For example, the first edge 2610 may be flat, without undulation, while the second edge 2612 undulates to follow or match the periphery of the patella, or vice versa. The first and/or second edges 2610, 2612 may be angled to match the facet angle of the native patella, or to match a desired angle between implant attachment surfaces, for example angle a seen in FIGS. 2F and 4E, angle c seen in FIG. 6A or angle d seen in FIG. 13. A window 2614 extends through the ring portion between the first edge 2610 and the second edge 2612. In the embodiment shown, the window 2614 is unitary and provides a patent, or unobstructed opening between the first and second edges 2610, 2612. The shape of the window is defined by the shape of the inner clamping surface 2604 of the clamp ring, and may be irregular or regular. Patient specific data may be used to determine the size and shape of the window 2614 and associated inner clamping surface 2604, in order to provide an optimal fit between the inner clamping surface 2604 and the patient's patella. The first and second edges may be annular.

The clamp ring 2600 can include at least one attachment feature 2606 shaped to allow attachment of the ring 2600 to the reaming guide 600. In other embodiments, the clamp ring 2600 may attach to the clamping apparatus 510, to the resection guide 1200, or to another patellar preparation instrument, in order to immobilize the patella during preparation procedures. The connection between the ring 2600 and the reaming guide 600 may be a snap connection with attachment feature 2606 snapping into a window or other opening or feature formed on the reaming guide. The attachment features 2606 may be offset from the ring body 2602 to allow maximum contact between the ring body 2602 and the patella 2 and associated patellar soft tissue. In the example in FIG. 29B, the attachment features project superiorly from the first edge 2612, although in other embodiments they may project inferiorly, medial-laterally, or not at all. The attachment features 2606 may be shaped to complement the window formed on the reaming guide, to prevent rotation of the clamp ring 2600 once attached to the reaming guide. In other embodiments, the attachment features may be bosses, projections, recesses, pegs, dovetails, grooves, screws, or other features which couple the clamp ring to the clamping apparatus. Once attached to the reaming guide or other instrument, the clamp ring and patella may be non-rotatably, rigidly attached and cannot move relative to the instrument.

Clamp ring 2600 may be referred to as a soft tissue clamping ring. Clamp ring 2600 may also clamp directly to hard tissue such as the bone, for example along the periphery 15 of the patella. When used with an anterior-posterior clamp such as shown in FIG. 28, the inner surface 2604 of the clamp ring 2600 clamps the perimeter of patella along a plane which is generally perpendicular to the anterior-posterior clamping provided by modular clamping apparatus 510. Thus, clamp ring 2600 may be used to stabilize and align the patella, while directly clamped to the bone surface. Use of clamp ring 2600 may also prevent rotation of the patella during reaming or other preparation processes. In use, the clamp ring 2600 may also encircle the soft tissue around the patella, so that the inner clamping surface 2604 of the ring 2600 conforms to the outer periphery 15 of the patella and suppresses the soft tissue around the patella, between the patella and the ring. These soft tissues may include the soft tissues inferior and superior to the patella.

Referring to FIGS. 30A and 30B, a patella is shown clamped in clamp ring 2600. The ring body 2602 encompasses the periphery 15 of the patella, circumferentially and rigidly clamping the patella and associated soft tissues. As disclosed above, dimensions of the ring body 2602 are determined by the measurements of the patella 2, so a conforming fit is formed between the patella and the ring body 2602. As seen in FIG. 30B, some or all of the anterior side 4 of the patella projects anteriorly beyond the second edge 2612, and some of the posterior side 6 of the patella may project posteriorly beyond the first edge 2610. Of course, the fit and relative anterior/posterior projection of each individual patella will vary.

Referring to FIGS. 31A and 31B, an alternate embodiment of a clamp ring is shown. Clamp ring 2600' includes the clamp body 2602 and attachment features 2606. A first resection slot 2620 is formed in one portion of the clamp body 2602, and a second resection slot 2622 is formed in another portion of the clamp body. The first resection slot may be referred to as a medial resection slot, and the second resection slot may be referred to as a lateral resection slot. The resection slots 2620, 2622 may be used as guides for a blade used to resect the patella in preparation for attaching an implant such as implant 100 or 200. In other embodiments, the first 2610 and/or second 2612 edges may also be used as resection guides. The trajectories of the resection slots may be angled to match the facet angle of the native patella, or to match a desired angle between implant attachment surfaces, for example angle a seen in FIGS. 2F and 4E, angle c seen in FIG. 6A, or angle d seen in FIG. 13.

The clamp rings and dorsal clamp insert disclosed herein may comprise metal or metal alloy, plastic including PEEK (polyetheretherketone), Radel (polysulfone), or Ultem, among other suitable materials. The clamp ring may be rigid as disclosed herein; however a flexible clamp ring or at least a flexible ring body is contemplated within the scope of the disclosure.

In a method of use, a patella 2 may be inserted into the clamp ring 2600. The patella 2 is positioned in the window 2614, and the outer periphery 15 of the patella is encircled and clamped directly by the ring body 2602. Some of the soft tissue surrounding the patella may be captured and suppressed between the patella and the ring body. The patient-specific data used to manufacture the clamp ring 2600 creates a customized and tight fit between the patella and the ring. The clamp ring 2600 holds the patella in a fixed orientation relative to the ring body. Thus immobilized, the patella may then be modified to accept an implant. The clamp ring 2600 may be rigidly attached to a patellar preparation via attachment features 2606, holding the patella in a fixed orientation relative to the instrument. Referring to FIG. 28, the clamp ring 2600 may be attached to instrument assembly 2500 to rigidly hold the patella during a reaming procedure, to permit precise reaming of the patella with the reamer. The clamp ring 2600 may also be attached to resection assembly 100 to rigidly hold the patella during a resection procedure to permit precise resectioning.

The dorsal clamp insert 2700 is further illustrated in FIGS. 32A-32E. The dorsal clamp insert 2700 may also be described as an anterior clamp insert, as it provides alignment and clamping on the anterior side of the patella 2. The dorsal clamp insert 2700 includes an insert body 2701 having a first side 2702 which in the context of FIG. 32E appears as an upper side, and a second side 2704 which appears as a lower side and is opposite the first side 2702. An insert perimeter 2706 bounds the outer edge of the insert between the first and second sides 2702, 2704. The perimeter 2706 may include a straight perimeter portion 2708, which may be flat, and which may aid in aligning the clamp insert 2700 relative to the clamping apparatus 510. The second side 2704 includes a base surface 2710 which may be planar as shown, or in another embodiment may be non-planar, for example convexly curved, to fit on to anterior clamp 520. One or more blind slots 2712 may be formed on the second side 2704, and may interrupt the insert perimeter 2706. The second side 2704 may further include an attachment feature 2716 to provide snapping attachment to anterior clamp 520. In other embodiments, one or more attachment features 2716 may be present, and may comprise bosses, projections, recesses, pegs, dovetails, grooves, screws, or other features which releasably couple the clamp insert to the clamping apparatus. In an embodiment, the attachment feature 2716 may be absent.

The first side 2702 includes a clamping surface 2720. The topography of the clamping surface 2720 may be customized to match the patient's native patella surface, determined by patient specific imaging and measurements. The shape of the clamping surface 2720 may be formed to complement the shape of the dorsal, or anterior side 4 of the patella 2. When a patella is clamped in the clamping apparatus as in FIG. 28, the complementary clamping surface 2720 may advantageously distribute clamping pressure across the anterior surface of the patella. The customized clamp insert 2700 can precisely align with the transverse, coronal, and sagittal axes of the patella to eliminate patellar tilt and rotation. When a patella is clamped in clamp ring 2600 and clamp insert 2700 as in FIG. 28, both the periphery 15 and anterior side 4 of the patella are available as reference surfaces for clamping and bone removal procedures. It is also appreciated that the anterior clamp 520 itself may be customized using patient specific measurements to complement the anterior side of the patella, and used without the clamp insert.

The dual axis reaming guide 600 may also be customized to be patient specific. Measurement of a patient's patella may be obtained as set forth above, and used to manufacture a reaming guide specific to the patient. With reference to FIGS. 6A-6D, the angle b between the first collet axis 612 and the second collet axis 613 may be defined by patient specific measurements. The radial diameters of the first and second collet bores 608, 609 may be defined by patient specific measurements, and may vary from one another. The angle c between the medial and lateral segments 618, 620 of the posterior reaming clamp 606 may be determined by patient specific measurements. Additionally the profile of the collet's bone contacting interface at the distal end of collet bores 152, 154 can be customized to follow the exact profile of the native patella prior to preparation. This may ensure 100%, contact between instrumentation and anatomy leading to better patella retention.

A customized reamer may be manufactured to provide patient specific reaming. For example, the diameters of both the reamer head 706 and the distal cutting surface 710 may be determined by patient specific measurements. One reamer head with a diameter customized to match first collet bore 608 may be produced, as may a second reamer head with a diameter customized to match second collet bore 609.

The depth gauge assembly 750 may also be customized to be patient specific. Patient measurement may be taken to determine the optimal reaming depth. With reference to FIGS. 9B and 10, outer housing 752 can be further described as including a housing base 755, bottom surface 753 forms the outer bottom surface of the housing base 755 and a base top surface 757 forms the top surface of the housing base. The thickness of the housing base 755 is the distance between the bottom surface 753 and the top surface 757. When the depth gauge assembly is used in the patella reaming process as described previously, the thickness of the housing base determines the depth of reaming into the patella, and may be equal to the depth of reaming into the patella. Patient specific measurements can be used to determine the thickness of the housing base 755 to manufacture a patient specific depth gauge assembly. Two separate depth gauge assemblies with different housing base thicknesses may be manufactured for reaming a patient's medial and lateral patellar facets 18, 20. A relatively thicker housing base will produce a deeper reamed recess, and a relatively thinner housing base will produce a shallower reamed recess. For example, with reference to FIG. 22, reamed medial facet surface 36 may be deeper than reamed lateral facet surface 38, depending on the thickness of housing base 755 in the depth gauge assembly used to ream each particular patellar facet.

In addition to the reaming based instrumentation set, a patient specific instrumentation set utilizing a saw guide concept can also be manufactured and employed. Referring to FIGS. 13 and 15A, patient customized components of the resection assembly 1000 can be manufactured. Regarding the resection or cutting guide 1200, the trajectories of lateral facet resection slot 1204 and a medial facet resection slot 1206 may be customized to patient specific measurements to match those of the facet angles of the native patella to improve coverage and increase bone preservation. In addition, during use the depth of cuts, and the number of cuts can all be altered to improve the match to the patient anatomy. The lateral position of the medial ridge location (post-resection) can also be adjusted by customizing the saw cut trajectories. The number of saw cuts created by the instrumentation can also be adjusted in order to more exactly recreate the surface topology of the native patella.

Figure 16:
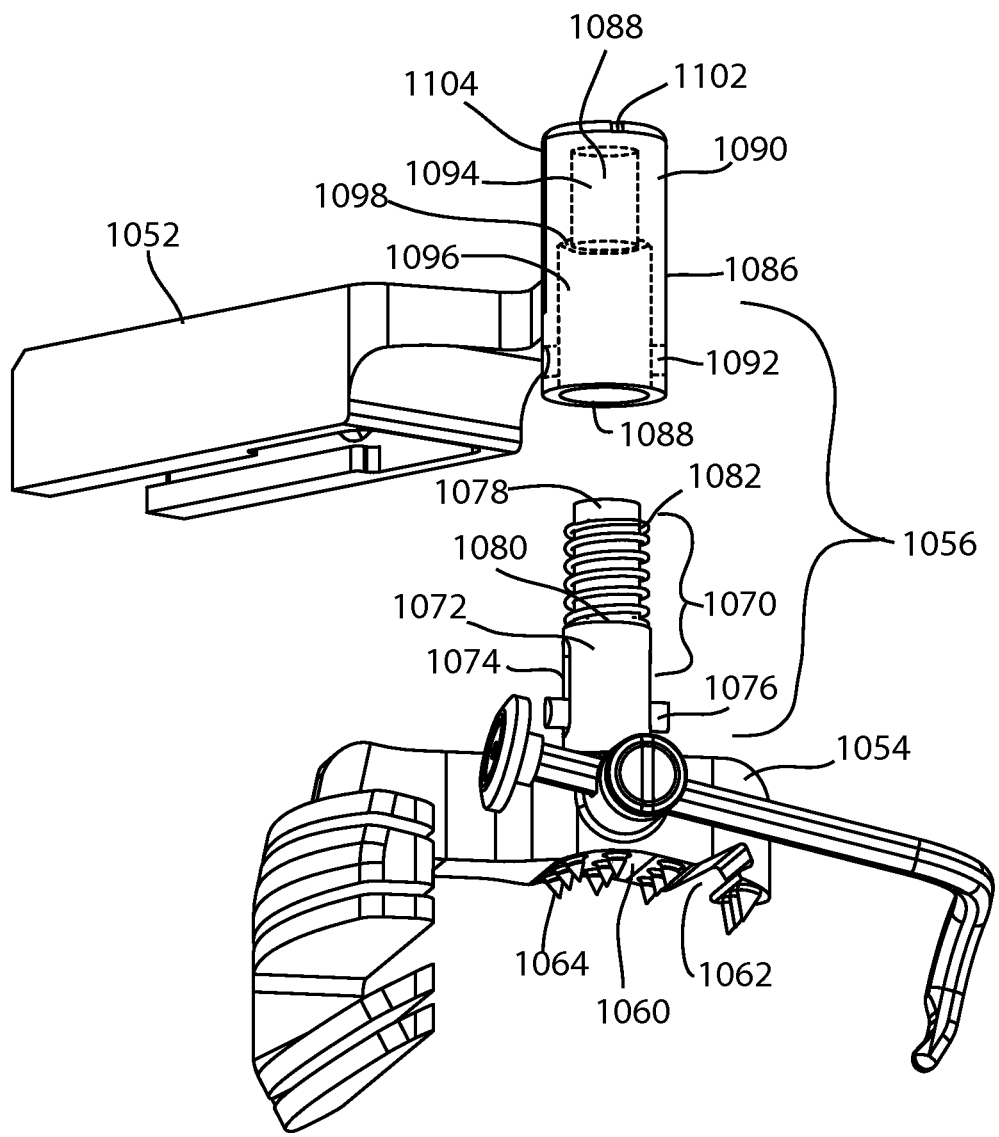
FIG. 16 is a partially exploded view of the force-limiting clamp assembly, adjustable restraint arm assembly, and resection cutting guide of FIG. 13, with dashed lines indicating interior features of a portion of the force-limiting clamp assembly.

In addition to customization of the cutting features, the means of restraining the patella can also be tailored. With reference to FIGS. 13 and 17, restraint arm 1164 may customized by varying its length, the curve of distal restraint end 1170, and the position of divot 1172 to best fit the outer profile of the patient's native patella, in order to stabilize the patella during clamping. With reference to FIGS. 13 and 16, the clamping surface 1060 of clamp body 154 can be customized to complement the shape of the posterior side of the patella. In one embodiment, the clamping surface may be customized to closely complement the exact topography of the posterior side; in another embodiment the clamping surface may be customized to complement the general curvature of the posterior side. In an embodiment, customized restraint arm 1164 and clamping surface 1060 are optimized for directly clamping on bone. In another embodiment, measurements including the soft tissues may be taken into account so that restraint arm 1164 and clamping surface 1060 are fabricated to clamp both soft tissues and bone for even greater restraint.

The patient specific instrumentation and implants disclosed herein allow for individualized bone preparation that may lead to one or more of the following advantages: improved implant fit; better coverage of the articular surface; more exact restorations of height and alignment; increased bone preservation; better patellar tracking; improved conformity at the patella-femoral joint; decreased patello-femoral joint wear; increased implant longevity; and reduced anterior knee pain It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, any patellar implant disclosed herein may be implanted onto a patellar prepared with any of the patellar preparation instrumentation or methods disclosed herein. Features of instrumentation from one example may be applied to instrumentation from another example. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for preparing a patient's patella to receive an implant, the system comprising:
a clamp ring for receiving and independently immobilizing the patella, the clamp ring comprising:
an annular ring body extending between a first edge and a second edge opposite the first edge, wherein the ring body is a continuous closed loop that defines and circumscribes an unobstructed opening extending between the first edge and the second edge, the closed loop having an integral continuous inner clamping surface for facing and contacting an outer periphery of the patella, the inner clamping surface extending between the first edge and the second edge around the interior of the closed loop to define and circumscribe the unobstructed opening;
wherein the inner clamping surface is customized based on measurements specific to the patient so that a shape of the clamping surface is such that the clamping surface faces and conformingly grips the outer periphery of the patella,
wherein the outer periphery of the patella is an outermost edge of the patella when viewed from a posterior or anterior view.

2. The system of claim 1, wherein the clamp ring further comprises an attachment feature for attaching the clamp ring to a patellar preparation instrument.

3. The system of claim 2, wherein the attachment feature protrudes from one of the first and second edges.

4. The system of claim 2, further comprising:
a reamer guide having a guiding structure for guiding a reamer;
wherein the clamp ring is rigidly coupled to the reamer guide, to permit precise reaming of the patella with the reamer.

5. The system of claim 2, further comprising a resection guide having a guiding structure for guiding a blade.

6. The system of claim 1, wherein at least one of the first edge and the second edge undulates to follow the outer periphery of the patella.

7. The system of claim 6, wherein the shape of the inner clamping surface is irregular, and is determined by the measurements specific to the patient.

8. The system of claim 1, wherein the shape of the ring body is non-circular.

9. The system of claim 1, wherein the first and second edges undulate.

10. The system of claim 1, wherein the clamp ring further comprises a straight slot extending through a portion of the ring body, the straight slot positioned for guiding a resection saw blade.

11. The system of claim 1, further comprising a dorsal clamp insert in contact with an anterior side of the patella, wherein a topography of the dorsal clamp insert is determined by patient specific imaging or measurements.

12. A system for preparing a patient's patella to receive an implant, the system comprising:
a retaining member for holding the patella in a fixed orientation, the retaining member comprising:
a continuous strip forming a closed loop, the closed loop having an upper edge and a lower edge, the closed loop defining an open window extending between the upper edge and the lower edge, the closed loop comprising an integral continuous retaining surface for facing and contacting an outer coronal periphery of the patella, the retaining surface extending between the upper edge and the lower edge around the interior of the closed loop to define and circumscribe the open window;

wherein the retaining surface is customized based on measurements specific to the patient so that a shape of the retaining surface is irregular such that the retaining surface faces and conformingly grips the outer coronal periphery of the patella, wherein the outer coronal periphery of the patella is an outermost edge of the patella when viewed from a posterior or anterior view.

13. The system of claim 12, wherein the retaining member further comprises at least one attachment feature for attaching the retaining member to a patellar preparation instrument in a fixed orientation relative to the instrument.

14. The system of claim 13, wherein the attachment feature protrudes from the upper edge of the closed loop.

* * * * *